United States Patent
Nakano et al.

(10) Patent No.: US 10,497,118 B2
(45) Date of Patent: Dec. 3, 2019

(54) IMAGE PROCESSING APPARATUS AND IMAGE PROCESSING METHOD OF A THREE-DIMENSIONAL MEDICAL IMAGE

(71) Applicant: CANON KABUSHIKI KAISHA, Tokyo (JP)

(72) Inventors: Yuta Nakano, juan-les-Pins (FR); Yoshio Iizuka, Kyoto (JP); Kiyohide Satoh, Kawasaki (JP); Gakuto Aoyama, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 4 days.

(21) Appl. No.: 16/029,169

(22) Filed: Jul. 6, 2018

(65) Prior Publication Data

US 2018/0315192 A1 Nov. 1, 2018

Related U.S. Application Data

(63) Continuation of application No. 13/556,310, filed on Jul. 24, 2012, now Pat. No. 10,049,445.

(30) Foreign Application Priority Data

| Jul. 29, 2011 | (JP) | 2011-167257 |
| Jun. 21, 2012 | (JP) | 2012-139507 |
| Jun. 21, 2012 | (JP) | 2012-139508 |

(51) Int. Cl.
*G06K 9/00* (2006.01)
*G06T 7/00* (2017.01)
(Continued)

(52) U.S. Cl.
CPC .......... *G06T 7/0012* (2013.01); *G06F 19/321* (2013.01); *G16H 15/00* (2018.01);
(Continued)

(58) Field of Classification Search
CPC ............. G06T 7/0012; G06T 7/33; G06T 2207/30004; G06T 7/73; G06F 17/30247;
(Continued)

(56) References Cited

U.S. PATENT DOCUMENTS

| 7,072,435 B2 | 7/2006 | Metz et al. |
| 7,894,676 B2 | 2/2011 | Iizuka et al. |

(Continued)

FOREIGN PATENT DOCUMENTS

| JP | H03-027485 A | 2/1991 |
| JP | 3085724 B2 | 9/2000 |

(Continued)

OTHER PUBLICATIONS

Extended European Search Report dated Apr. 22, 2013 in counterpart European Patent Application No. 12178176.9.

(Continued)

*Primary Examiner* — Vu Le
*Assistant Examiner* — Guillermo M Rivera-Martinez
(74) *Attorney, Agent, or Firm* — Venable LLP

(57) ABSTRACT

A user had to manually select a cross-sectional image indicating features of a finding and a cross-sectional image displayed in a report, from a three-dimensional medical image. Provided is an image processing apparatus that includes: a unit configured to acquire a target finding of a medical image; a unit configured to calculate an image feature quantity of a type associated in advance with the target finding, for each of a plurality of cross-sectional images of the medical image; and a unit configured to identify a cross-sectional image from the plurality of cross-sectional images based on the calculated image feature quantity. Operation of selecting a cross-sectional image by a doctor can be omitted, and the burden can be reduced.

13 Claims, 15 Drawing Sheets

(51) Int. Cl.
*G06F 19/00* (2018.01)
*G16H 40/63* (2018.01)
*G16H 15/00* (2018.01)
*G16H 30/20* (2018.01)
*G16H 30/40* (2018.01)

(52) U.S. Cl.
CPC .............. *G16H 30/20* (2018.01); *G16H 30/40* (2018.01); *G16H 40/63* (2018.01); *G06T 2207/10072* (2013.01); *G06T 2207/20108* (2013.01); *G06T 2207/30004* (2013.01)

(58) Field of Classification Search
CPC .............. G06F 3/0482; G06K 2209/05; G06K 9/00288; G06K 9/3233
See application file for complete search history.

(56) References Cited

U.S. PATENT DOCUMENTS

| | | |
|---|---|---|
| 8,009,936 B2 | 8/2011 | Oosawa et al. |
| 2002/0057844 A1 | 5/2002 | Sirohey et al. |
| 2003/0013951 A1 | 1/2003 | Stefanescu et al. |
| 2004/0252870 A1 | 12/2004 | Reeves et al. |
| 2005/0020903 A1 | 1/2005 | Krishnan et al. |
| 2007/0092142 A1 | 4/2007 | Kuriathungal et al. |
| 2007/0160275 A1 | 7/2007 | Sathyanarayana |
| 2007/0237377 A1 | 10/2007 | Oosawa |
| 2008/0170771 A1 | 7/2008 | Yamagata et al. |
| 2008/0240494 A1* | 10/2008 | Oosawa ............ G06F 17/30259 382/100 |
| 2008/0292194 A1 | 11/2008 | Schmidt et al. |
| 2009/0028403 A1 | 1/2009 | Bar-Aviv et al. |
| 2009/0161937 A1 | 6/2009 | Peng et al. |
| 2010/0106002 A1 | 4/2010 | Sugiyama et al. |
| 2010/0189366 A1 | 7/2010 | Iizuka et al. |
| 2010/0191685 A1* | 7/2010 | Sapir .................. G06K 9/623 706/13 |
| 2010/0284590 A1 | 11/2010 | Peng et al. |
| 2011/0199390 A1 | 8/2011 | Iizuka et al. |
| 2011/0262015 A1 | 10/2011 | Ishikawa et al. |
| 2011/0268331 A1* | 11/2011 | Binning ............ G06F 19/321 382/131 |
| 2012/0088981 A1 | 4/2012 | Liu et al. |
| 2012/0136882 A1 | 5/2012 | Kawagishi et al. |
| 2012/0250961 A1* | 10/2012 | Iwasaki ............ G06F 19/321 382/128 |
| 2012/0262460 A1 | 10/2012 | Endo et al. |
| 2013/0338496 A1* | 12/2013 | Hielscher ............ A61B 5/0064 600/425 |

FOREIGN PATENT DOCUMENTS

| | | |
|---|---|---|
| JP | 2004-351056 A | 12/2004 |
| JP | 2007-143982 A | 6/2007 |
| JP | 2009-82443 A | 4/2009 |
| JP | 2009-207541 A | 9/2009 |
| JP | 2011-123574 A | 6/2011 |
| JP | 2011-206155 A | 10/2011 |
| WO | 01/57777 A2 | 8/2001 |
| WO | 2007/096214 A1 | 8/2007 |
| WO | 2010/018488 | 2/2010 |
| WO | 2010/109351 | 9/2010 |

OTHER PUBLICATIONS

J. Sinha, et al., "Image Study Summarization of MR Brain Images by Automated Localization of Relevant Structures", Ann. N.Y. Acad. Sci. 980: 278-286 (2002).

Communication dated Jul. 11, 2016, in corresponding EP application No. 12178176.9 (7 pages).

Yuan et al., "Diagnosis system of computer-aided brain MRI using content-based image retrievel", May 2008, Proceedings of the 5th International Conference on Information Technology and Application in Biomedicine, in conjunction with the 2nd International Symposium & Summer School on Biomedical and Health Engineering, pp. 152-156.

Sato et al., "Innovation of PACS for computer aided diagnosis with functions to assist comparative reading for lung cancer based on multi-helical CT images", May 2003, Proceedings of SPIE, Medical Imaging 2003: PACS and Integrated Medical Information Systems: Design and Evaluation, vol. 5033, pp. 413-423.

* cited by examiner

IMAGE PROCESSING APPARATUS AND IMAGE PROCESSING METHOD OF A THREE-DIMENSIONAL MEDICAL IMAGE

The present application is a continuation of U.S. patent application Ser. No. 13/556,310, filed Jul. 24, 2012, which claims priority to JP 2011-167257, filed Jul. 29, 2011; JP 2012-139507, filed Jun. 21, 2012; and JP 2012-139508, filed Jun. 21, 2012, the entire disclosure of each of which is incorporated by reference herein.

BACKGROUND OF THE INVENTION

Field of the Invention

The present invention relates to a technique for processing and displaying three-dimensional medical image data.

Description of the Related Art

Three-dimensional volume data is the mainstream of medical image data of recent years. In diagnostic imaging, a doctor consecutively switches and displays (scroll display) cross-sectional images to check whether there is an abnormal shadow. When the doctor finds an abnormal shadow in the diagnostic imaging, the doctor repeatedly scrolls and displays cross-sectional images around the cross-sectional images including the abnormal shadow and adjusts display parameters to figure out features of the abnormal shadow based on detailed observation. The doctor inputs the features of the abnormal shadow as imaging findings and selects a cross-sectional image that represents the abnormal shadow (for example, a cross-sectional image with the largest abnormal shadow) to organize a report by attaching the cross-sectional image.

In diagnostic imaging, more detailed diagnosis has become possible by the formation of three-dimensional image data. However, the doctor needs to select a cross-sectional image from three-dimensional image data to display a two-dimensional cross-sectional image or to organize a report, and the burden of the doctor is increasing. Inventions for reducing the burden of the doctor in the series of operations have been proposed. Japanese Patent Application Laid-Open No. 2007-143982 proposes a method of automatically adjusting display parameters based on image feature quantities in a region of interest. Furthermore, an example of a general method includes a method of obtaining the center of gravity of a region of interest in three-dimensional image data to display cross-sectional images of cross sections passing through the center of gravity.

In recent years, an inference technique of an image diagnosis using an SVM (Support Vector Machine), an ANN (Artificial Neural Network) or a Bayesian network is studied. The doctor can refer to the image diagnosis calculated using the inference technique, and an effect of improving the reliability of the image diagnosis can be expected.

However, Japanese Patent Application Laid-Open No. 2007-143982 is directed to an arrangement for adjusting the display parameters according to the situations in a checkup or in a thorough examination, and cross-sectional images cannot be selected from the three-dimensional image data in this arrangement. Even if the method of selecting a cross-sectional image passing through the center of gravity of a region of interest in the three-dimensional image data is used to select the cross-sectional image to be displayed, the cross-sectional image may not always be the cross-sectional image representing the abnormal shadow. Eventually, the doctor needs to select the cross-sectional image, and the burden of the doctor cannot be reduced.

As described, the doctor determines the imaging finding and the image diagnosis based on knowledge and experience of the doctor, and there is a problem that the determination is not always highly objective. The doctor usually performs the diagnostic imaging alone, and it is difficult for the doctor to notice that the doctor has overlooked or falsely observed an imaging finding. Therefore, there is a problem that the diagnosis is not always highly reliable. An effect of reducing the oversight of an abnormal shadow can be expected using a technique of Japanese Patent No. 3085724. An effect of improving the reliability of the image diagnosis can also be expected using the inference technique. However, in any of the related art, support information for improving the objectivity and the reliability of an imaging finding related to a discovered abnormal shadow cannot be obtained.

SUMMARY OF THE INVENTION

The present invention has been made in view of the foregoing problems. According to one embodiment of the present invention, a cross-sectional image indicating a feature of an acquired finding is selected from three-dimensional medical image data and displayed. The present invention provides an image processing apparatus including: a target finding acquisition unit configured to acquire a target finding of a medical image; a feature quantity calculation unit configured to calculate an image feature quantity of a type associated in advance with the target finding, for each of a plurality of cross-sectional images of the medical image; and a cross-sectional image identification unit configured to identify one of the plurality of cross-sectional images based on the calculated image feature quantity.

Another embodiment of the present invention provides a diagnostic imaging apparatus including: an imaging finding acquisition unit configured to acquire, from a user, a type and an evaluation value of an imaging finding related to a predetermined three-dimensional region of a three-dimensional image to be diagnosed; a characteristic value calculation unit configured to calculate a characteristic value that can be compared with the evaluation value of the imaging finding based on an image feature, from each of a plurality of cross-sectional images included in the predetermined three-dimensional region; a representative characteristic value calculation unit configured to calculate a representative characteristic value that represents the predetermined three-dimensional region from a plurality of characteristic values calculated from the plurality of cross-sectional images; a representative cross-sectional image acquisition unit configured to acquire a cross-sectional image, in which the representative characteristic value is calculated, as a representative cross-sectional image from the plurality of cross-sectional images; a comparison unit configured to compare the evaluation value of the imaging finding and the representative characteristic value; and a display unit configured to display the representative cross-sectional image only if a comparison result of the comparison unit indicates a significant difference.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Exemplary embodiments of an image processing apparatus and a control method of the image processing apparatus according to the present invention will now be described with reference to the attached drawings. However, the scope of the invention is not limited to the illustrated examples.

[First Embodiment]

A configuration of an image processing apparatus 1 according to the present embodiment will be described with reference to FIG. 1. In the image processing apparatus 1, a three-dimensional medical image acquisition unit 1001 acquires an image from a database 2. A target finding acquisition unit 1002 acquires a target imaging finding after interpretation of radiogram of the image by the user. In the present embodiment, the imaging finding acquired by the target finding acquisition unit 1002 is set as a target finding. A feature type identification unit 1003 identifies an image feature type to be calculated based on the acquired target finding. A feature quantity calculation unit 1004 calculates the identified image feature quantity. A cross-sectional image identification unit 1005 calculates cross-sectional image selection indexes in the cross-sectional images and determines a cross-sectional image based on the cross-sectional image selection indexes. Lastly, a display control unit 1006 displays the specified cross-sectional image.

Figure 2:
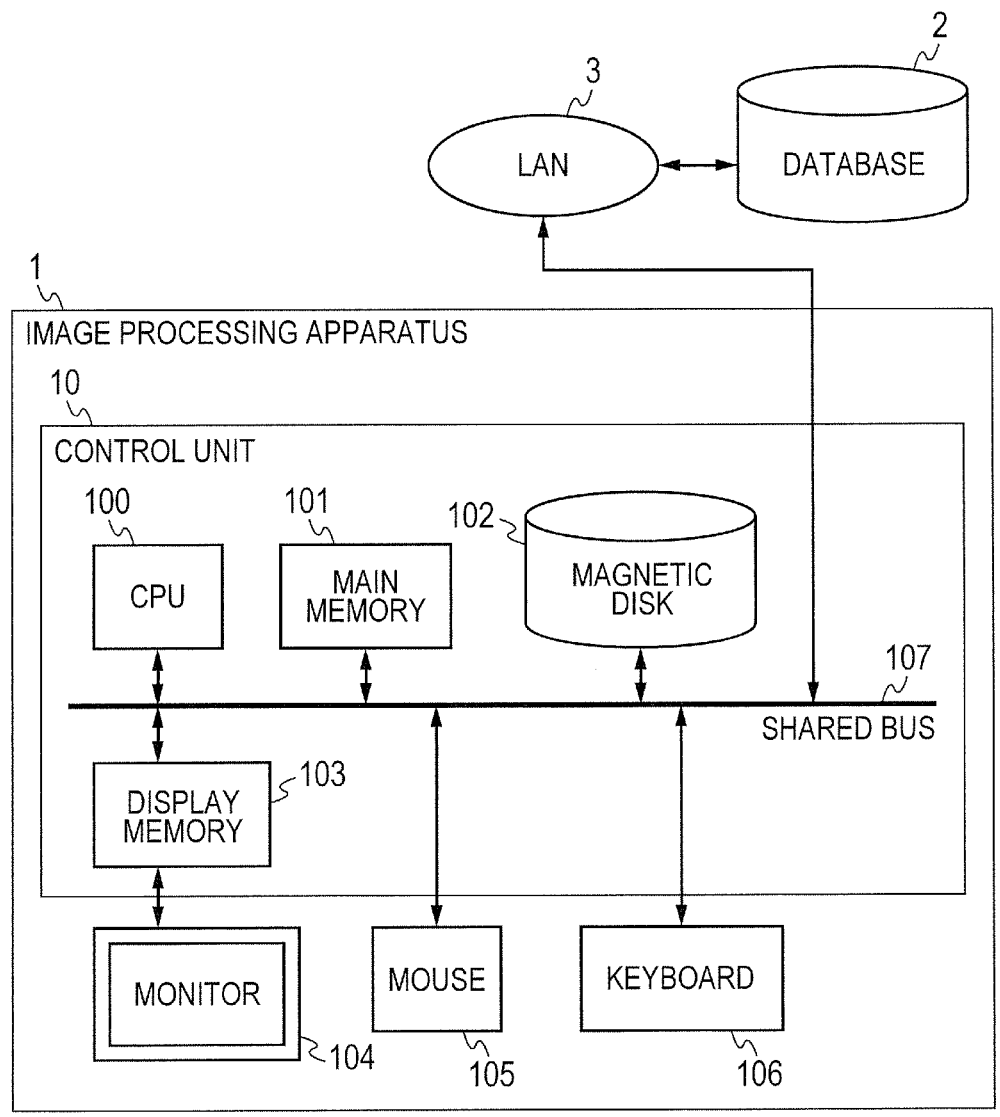
FIG. 2 is a diagram illustrating a basic configuration of a computer that realizes components of the image processing apparatus by software.

FIG. 2 is a diagram illustrating a configuration example when a computer realizes the image processing apparatus according to the first embodiment. The image processing apparatus 1 includes a control unit 10, a monitor 104, a mouse 105 and a keyboard 106. The control unit 10 includes a central processing unit (CPU) 100, a main memory 101, a magnetic disk 102 and a display memory 103. The CPU 100 executes a program stored in the main memory 101 to perform various controls, such as communication with the database 2 and overall control of the image processing apparatus 1. The CPU 100 mainly controls operations of the constituent elements of the image processing apparatus 1. The main memory 101 stores a control program executed by the CPU 100 and provides an operation region for the CPU 100 to execute the program. The magnetic disk 102 stores various types of application software including programs for executing an operating system (OS), a device drive of a peripheral device and a diagnosis supporting process described later. The display memory 103 temporarily stores display data according to the display control unit 1006. The monitor 104 is, for example, a CRT monitor or a liquid crystal monitor, and the monitor 104 displays an image based on data from the display memory 103. The mouse 105 and the keyboard 106 are for pointing input and input of characters by the user (doctor). A shared bus 107 interconnects the constituent elements to allow communication.

In the present embodiment, the image processing apparatus 1 can read out medical image data from the database 2 through a LAN (Local Area Network) 3. An existing PACS (Picture Archiving and Communicating System) can be used as the database 2. Examples of the types of the three-dimensional medical image data include an X-ray CT image, an MRI image, a PET image and a SPECT image.

A general computer and peripheral devices of the computer can be used to form the device configuration. A control procedure of the image processing apparatus according to the present invention described later with reference to FIG. 4 can be realized as a computer program executed on the computer.

Figure 3:
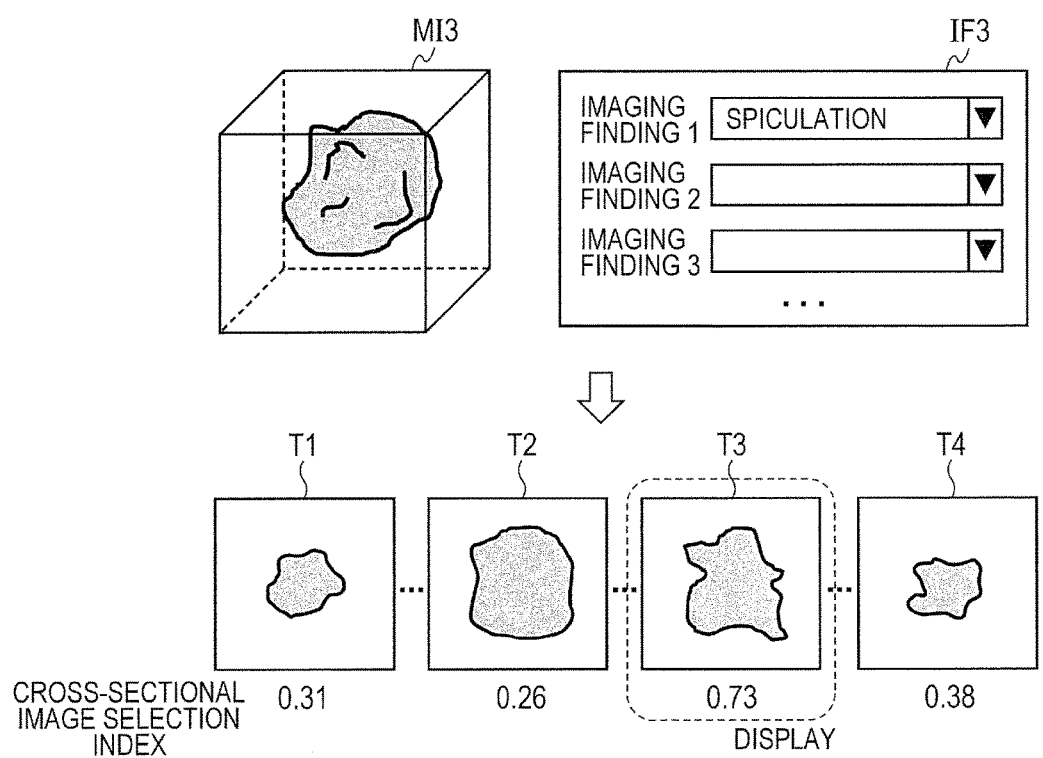
FIG. 3 is a diagram illustrating a summary of a process of the image processing apparatus according to the first embodiment.

FIG. 3 illustrates a summary of image processing of the present embodiment. In FIG. 3, "MI3" denotes a three-dimensional medical image to be diagnosed and is input from a database. An example of a chest X-ray CT image will be illustrated in the present embodiment, and a processing apparatus used to determine the presence/absence of an abnormal shadow or to diagnose features will be described. "IF3" denotes an imaging finding input area, and imaging findings can be input from a pull-down menu. When an imaging finding is input, a type of an image feature quantity associated in advance with the imaging finding is identified. The image feature quantities are calculated for the cross-sectional images, and cross-sectional image selection indexes are further calculated from the image feature quantities. A cross-sectional image indicating the feature of the input imaging finding is selected according to the cross-sectional image selection indexes. In FIG. 3, "Spiculation" is input as the imaging finding, and the cross-sectional image selection indexes are calculated from the image feature quantities associated in advance with the "Spiculation". A cross-sectional image T3 is selected based on the calculation result.

Figure 4:
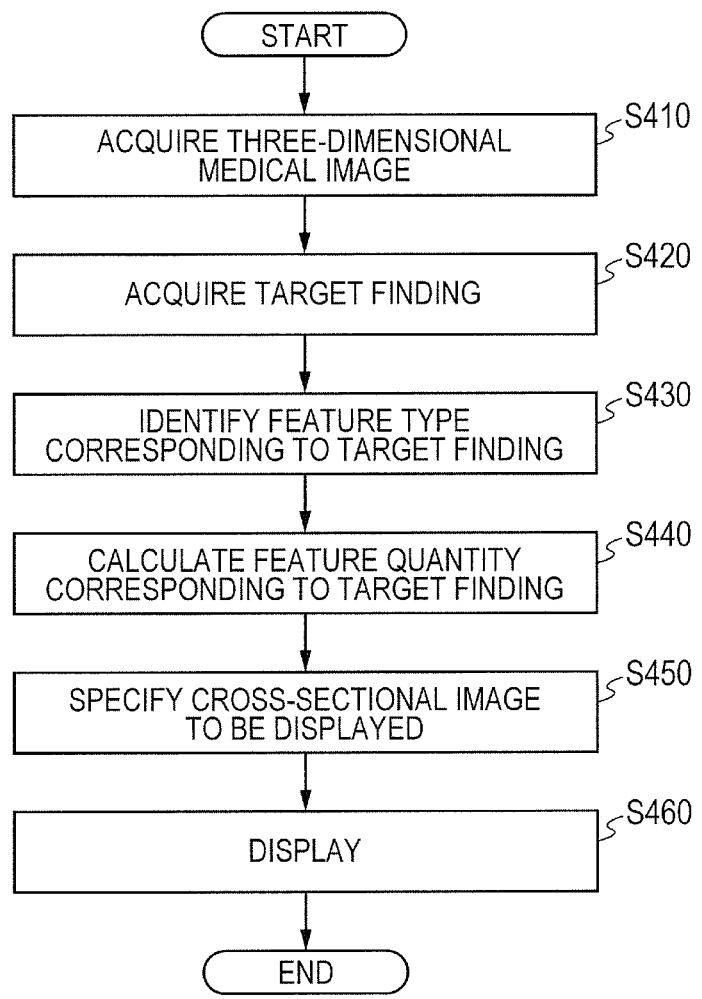
FIG. 4 is a flow chart illustrating a processing procedure of the first embodiment of the image processing apparatus.

FIG. 4 is a flow chart of the present embodiment. A specific processing procedure executed by the image processing apparatus 1 will be described with reference to the flow chart.

Step S410

In step S410, the three-dimensional medical image acquisition unit 1001 acquires a three-dimensional medical image from the database 2. In the present embodiment, the acquired image may be used in a process of a later stage, or the user may designate a region of interest (ROI) to limit the region of the image. When the region is limited, for example, the region may be designated from the three-dimensional medical image through a GUI not illustrated, and the region may replace the three-dimensional medical image handled in a process of a later stage.

Step S420

In step S420, the target finding acquisition unit 1002 acquires, as a target finding, an imaging finding input by the user through the GUI not illustrated in relation to the three-dimensional medical image. In the present embodiment, the user diagnoses the acquired three-dimensional medical image and uses an imaging finding input form as illustrated by "IF3" of FIG. 3 to input the imaging finding. Examples of the imaging findings that can be input include "Round", "Spiculation" and "Ill-defined border". The user inputs at least one of the imaging findings. The method of selecting the imaging finding is not limited to this. For example, if a past diagnosis result of the same patient is stored in the database, the imaging finding input in the diagnosis result may be used as the target finding.

Step S430

In step S430, the feature type identification unit 1003 identifies the types of the image feature quantities calculated based on the target finding obtained by the target finding acquisition unit 1002. In the present embodiment, the types of the image feature quantities are associated in advance with the imaging findings, and the types of the image feature quantities to be calculated are automatically determined from the selected target finding. An example of association between the imaging findings and the image feature types is as follows.

"Round": circularity C, aspect ratio A
"Spiculation": contour line length L, filling factor F
"Ill-defined border": sum E of border edge components Step S440

In step S440, the feature quantity calculation unit 1004 calculates the image feature quantities, the types of which are identified in step S430, for the cross-sectional images of the three-dimensional medical image based on the target finding obtained by the target finding acquisition unit 1002.

The circularity C, the aspect ratio A, the contour line length L and the filling factor F are calculated from a binary image generated from the three-dimensional medical image. To generate the binary image in the present embodiment, a threshold is determined by discriminant analysis from a histogram of the three-dimensional medical image, and a binarization process is applied. The circularity C, the aspect ratio A and the filling factor F are calculated by the following formulas using the generated binary image.

Circularity $$C = 4\pi * \left(\frac{\text{Area}}{L^2}\right) \quad (1)$$

Aspect Raito $$A = \begin{cases} \dfrac{Feret_h}{Feret_v} & (Feret_v > Feret_h) \\ \dfrac{Feret_v}{Feret_h} & (Feret_h > Feret_v) \end{cases} \quad (2)$$

Filling Factor $$F = \frac{\text{Area}}{Feret_h * Feret_v} \quad (3)$$

"Area" denotes an area of each region in the binary image. "$Feret_h$" denotes a horizontal direction Feret diameter, and "$Feret_v$" denotes a vertical direction Feret diameter. The Feret diameters are calculated from a bounding rectangle of each region in the binary image. If there is a plurality of regions in the binary image, a region with the largest area is set as a target region in the present embodiment, and the image feature quantities are calculated. The contour line length L denotes a length of a contour line of the target region. The sum E of edge components denotes a sum of the edge components on the contour line of the target region. The edge components denote components obtained by applying a Sobel filter to the three-dimensional medical image.

In the calculation method, the image feature quantities associated with the target finding are calculated in the cross-sectional images. In the present embodiment, the image feature quantities are calculated for cross-sectional images in axial, coronal and sagittal cutting directions (for example, cross-sectional images generated at 1 mm intervals). The method of selecting the cross-sectional images for calculating the image feature quantities is not limited to this. For example, the cutting directions of the cross-sectional images are not limited to axial, coronal and sagittal, and the cross-sectional images may be created in free cutting directions. For example, an x axis, a y axis and a z axis passing through the center of the image may be set, and one or two of the axes may be set as rotation centers. The image feature quantities may be calculated from cross-sectional images in cutting directions obtained by rotating the image by 10 degrees each for 180 degrees.

Step S450

In step S450, the cross-sectional image identification unit 1005 determines a cross-sectional image indicating the feature of the target finding based on the image feature quantities calculated by the feature quantity calculation unit 1004. In the present embodiment, values of the cross-sectional images indicating "degrees indicating the target finding" are calculated (digitized) from the image feature quantities calculated in step S440, and the values are set as "cross-sectional image selection indexes" based on the target finding. The following is an example of formulas for calculating the cross-sectional image selection indexes corresponding to the three imaging findings.

Round Index $$I_{sp} = w_1 * C + w_2 * A \quad (4)$$

Spiculation Index $$I_{su} = w_3 * L - w_4 * F \quad (5)$$

Border Irregular Index $$I_{co} = w_5 * E \quad (6)$$

Here, "w" denotes a predetermined weight. In the present embodiment $w_1$ to $w_5 = 1.0$.

A selection standard other than the "degrees indicating the target finding" may be incorporated into the formulas of the index calculation. For example, an item indicating the size of the region in the binary image or the closeness to the center of gravity of the region of interest may be added to the formulas to take into account the standard other than the target finding.

The formulas are used to calculate, for each cross-sectional image, the cross-sectional image selection indexes corresponding to the target finding. The cross-sectional image with the maximum cross-sectional image selection index is determined as the cross-sectional image to be displayed. If a plurality of findings is selected in step S420, the cross-sectional image selection indexes are calculated for all selected target findings in the present embodiment, and the cross-sectional image with the greatest total value of the indexes is determined as the cross-sectional image to be displayed. The cross-sectional image is stored as data for the report.

Step S460

In step S460, the display control unit 1006 displays the cross-sectional image identified by the cross-sectional image identification unit 1005.

In this way, the cross-sectional image to be displayed can be selected based on the image feature quantities associated with the imaging finding to automatically select the cross-sectional image indicating the feature of the input imaging finding.

In the description, if there is a plurality of target findings in step S450, the cross-sectional image selection indexes of each target finding are calculated, and the cross-sectional image is determined from the total value. However, the cross-sectional images that maximize the cross-sectional image selection indexes may be selected, and the cross-sectional images may be displayed in association with the target findings. In this case, the user may be able to select a cross-sectional image to be used in the report.

[Second Embodiment]

The present embodiment describes an example of calculating the image feature quantities from the three-dimensional medical image to automatically select the target finding, without using the instruction of the user in the input of the imaging finding. The imaging finding that is likely to be included in the image can be identified based on the image feature quantities calculated from the acquired image, and the imaging finding can be automatically selected as the target finding.

The configuration of the apparatus is similar to that of the first embodiment, and the description will not be repeated. However, the difference from the first embodiment is that the target finding acquisition unit 1002 automatically selects the target finding from the three-dimensional medical image. Another difference is that when the image processing apparatus 1 operates based on a command of software, a program stored in a ROM or an HDD is a program for executing a process of FIG. 5 and for realizing a function of the process.

Figure 5:
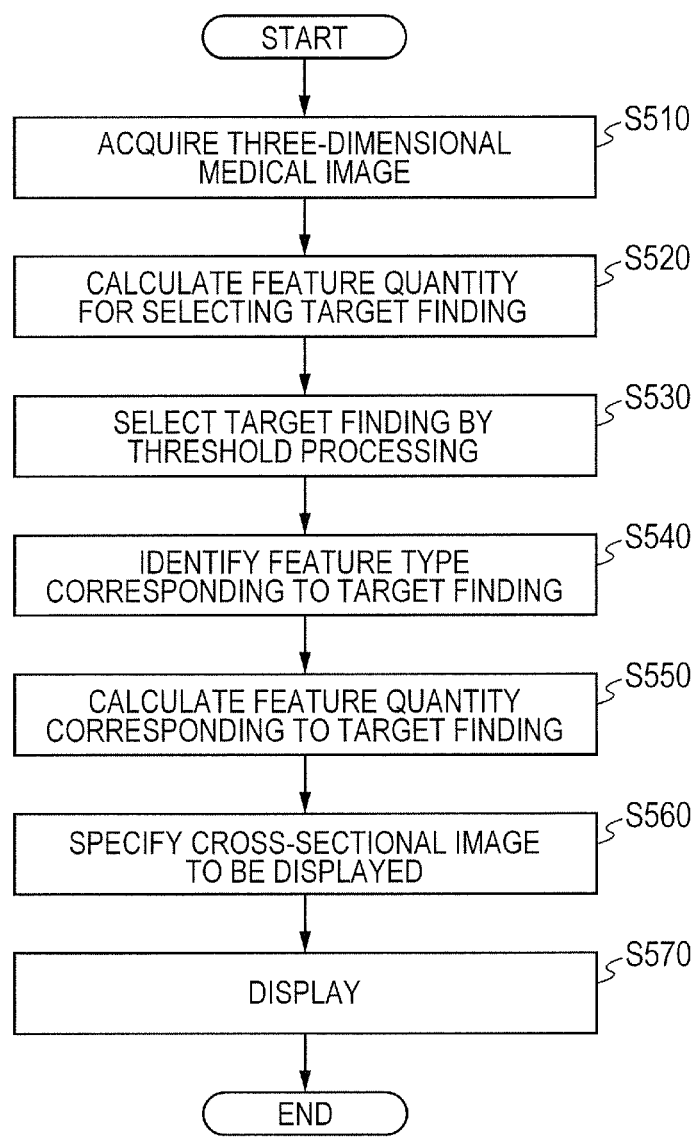
FIG. 5 is a flow chart illustrating a processing procedure of a second embodiment of the image processing apparatus.

Details of steps S520 and S530 according to a second embodiment will be described with reference to FIG. 5. The process of step S510 and steps S540 to S570 is the same as the process of step S410 and steps S430 to S460 in the flow chart of FIG. 4 of the first embodiment, and the description will not be repeated.

Step S520

In step S520, the target finding acquisition unit 1002 calculates feature quantities for selecting the target finding from the three-dimensional medical image acquired by the three-dimensional medical image acquisition unit 1001.

In the present embodiment, all types of cross-sectional image selection indexes are calculated in each cross-sectional image using formulas (4) to (6) of step S450. The cross-sectional image selection indexes calculated from each cross-sectional image are added for all cross-sectional images to set the feature quantities for selecting the target finding. More specifically, in the present embodiment, all prepared types of indexes, such as a round index, a lobular shape index, an irregular shape index, a spiculation index and a border irregular index, are calculated in each three-dimensional medical image, and values obtained by adding the indexes for all cross-sectional images are calculated as the feature quantities. The calculation method of the feature quantities for selecting the target finding is not limited to this. For example, the maximum values of the indexes calculated in each cross-sectional image may be used as the feature quantities for selecting the target finding.

Step S530

In step S530, the target finding acquisition unit 1002 identifies the imaging finding that is likely to be included in the image based on the feature quantities for selecting the target finding calculated in step S520 and selects the imaging finding as the target finding.

In the present embodiment, threshold processing is applied to the feature quantities for selecting the target finding calculated in step S520 to select the imaging finding of the three-dimensional medical image. A threshold is set in advance for each feature quantity, and the imaging finding corresponding to the feature quantity greater than the threshold is selected as the target finding. If there is a plurality of feature quantities greater than the thresholds, all of the feature quantities are handled as the target findings, and the process moves to the next step. However, if a plurality of imaging findings belonging to the same category (for example, the imaging findings belonging to the category of "Shape" are "Spherical", "Lobular" and "Irregular") is selected, the imaging finding with the maximum feature quantity is selected to set the target finding. The selection method of the imaging finding is not limited to this. For example, the imaging finding may be selected from the feature quantities by constructing an identifier by Support Vector Machine or AdaBoost based on learning using sets of the feature quantities and the imaging findings obtained for past diagnosis results.

In this way, the selection of the target finding from the feature quantities automates the input operation of the imaging finding by the doctor. Therefore, the process from the input of the imaging finding to the display of the cross-sectional image indicating the feature of the imaging finding is all automated.

[Third Embodiment]

In the present embodiment, the target finding is acquired using the method of the first or second embodiment. An inference unit is used to perform differential diagnosis, and a cross-sectional image indicating the feature of a target finding contributed to the diagnosis is displayed. It is assumed in the present embodiment that the doctor has input imaging findings other than the target finding.

The configuration of the apparatus is similar to that of the first embodiment, and the description will not be repeated. However, the difference from the first embodiment is that the target finding acquisition unit 1002 automatically selects the target finding from a large number of imaging findings. Another difference is that when the image processing apparatus 1 operates based on a command of software, a program stored in a ROM or an HDD is a program for executing a process of FIG. 6 and for realizing a function of the process.

Figure 6:
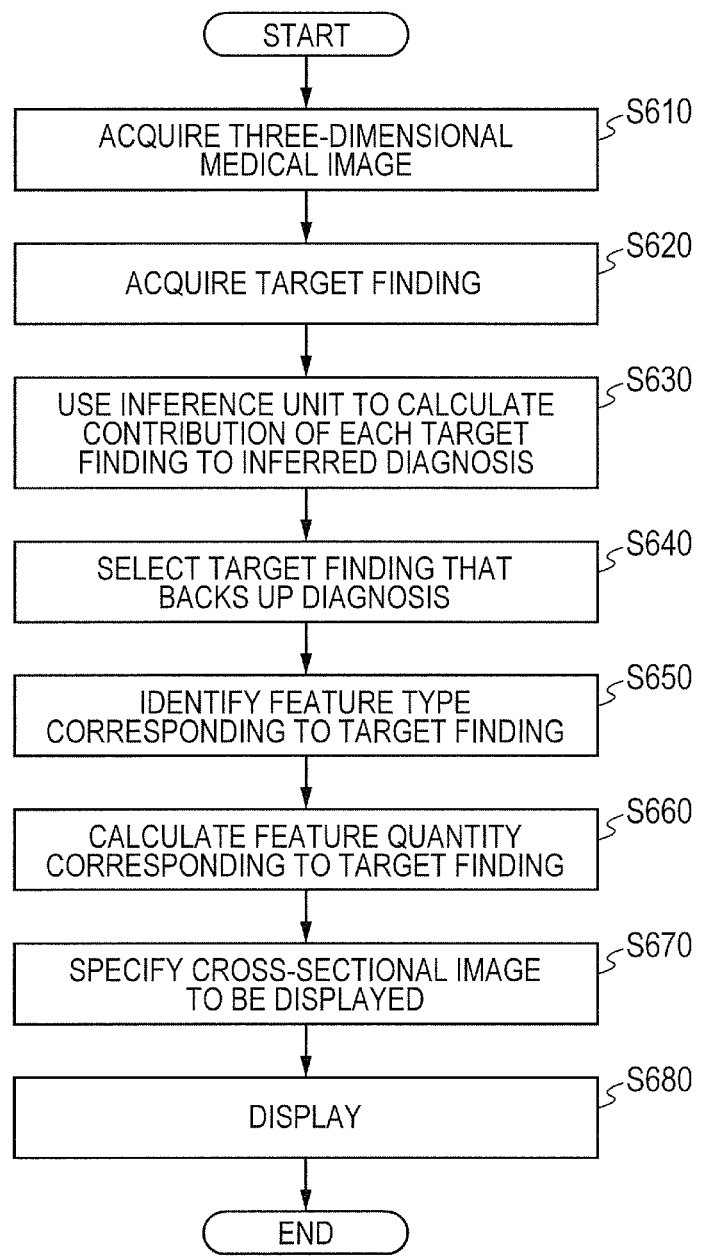
FIG. 6 is a flow chart illustrating a processing procedure of a third embodiment of the image processing apparatus.

Details of steps S630 and S640 according to a third embodiment will be described with reference to FIG. 6. The process of steps S610, S620 and S650 to S680 is the same as the process of steps S410, S420 and S430 to S460 in the flow chart of FIG. 4 of the first embodiment, and the description will not be repeated.

Step S630

In step S630, the target finding acquisition unit 1002 inputs all acquired imaging findings to the inference unit. An existing inference method, such as the Bayesian network and the neural network, can be used for the inference. In the present embodiment, the Bayesian network is used for the inference. The Bayesian network is an inference model using conditional probability. When the Bayesian network is applied to the present embodiment, the imaging finding is handled as an input, and inferred probability of each diagnosis can be acquired. The diagnoses handled in the present embodiment are "primary lung cancer", "lung metastasis" and "etc."

In the present embodiment, when each diagnosis is defined as "$D_i$" and each finding is defined as "$S_j$", contribution of "$S_j$" is calculated using a difference between a prior probability $P(D_i)$ (probability of each diagnosis when there is no input) and a probability $P(D_i|S_j)$ when only "$S_j$" is input. For example, contribution $C(D_i|S_j)$ of the finding $S_j$ to the diagnosis $D_i$ can be expressed by the following formula.

$$C(D_i|S_j)=P(D_i|S_j)-P(D_i) \quad (7)$$

The contribution in each diagnosis is calculated for all imaging findings prepared as choices. In the present embodiment, the contribution of each imaging finding in the diagnosis with the highest probability (inferred diagnosis) in the inference result based on the Bayesian network is transmitted to the next step.

Step S640

In step S640, the target finding acquisition unit 1002 selects the target finding according to the contribution calculated in step S630. In the present embodiment, threshold processing is applied to the contribution calculated in step S630 to select the target finding. A threshold is set in advance for the contribution, and the target finding with the contribution greater than the threshold is selected. If there is a plurality of target findings with the contribution greater than the threshold, all of the target findings are selected. If there is no target finding with the contribution greater than the threshold, the target finding with the maximum contribution is selected. Other than the selection method, the target finding with the maximum contribution may be selected without using the threshold.

In this way, the cross-sectional image indicating the feature of the imaging finding that backs up the inference result can be displayed by selecting the target finding based on the contribution to the diagnosis obtained from the inference unit.

In the description, the contribution is calculated in the diagnosis with the highest probability in the inference result based on the Bayesian network to select the target finding in step S630. However, the target finding may be selected based on the contribution in the diagnosis input by the user (doctor). Specifically, if the diagnosis input as an impression by the doctor and the diagnosis inferred by the Bayesian network are different, the target finding may be selected based on the contribution to the diagnosis selected by the doctor. This can attain an effect of selecting a cross-sectional image indicating the imaging finding that describes the ground of the diagnosis by the doctor.

According to the embodiment of the present invention, the cross-sectional image indicating the feature of the target imaging finding can be automatically selected and displayed. As a result, the burden of the doctor can be reduced.

Figure 7:
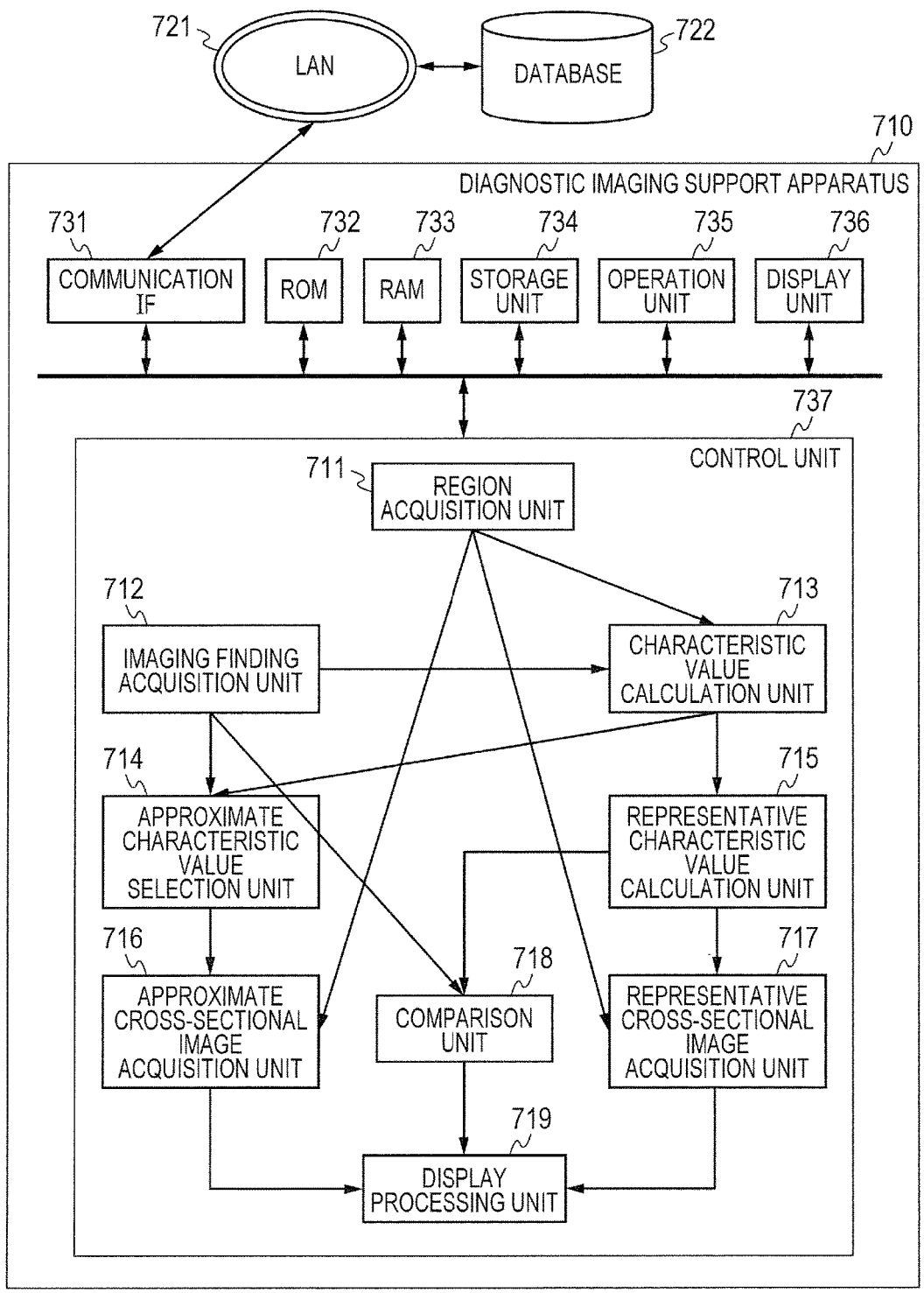
FIG. 7 is a diagram illustrating an example of an overall configuration of a diagnostic imaging support system including a diagnostic imaging support apparatus according to an embodiment of the present invention.

Another embodiment of the present invention will be described. FIG. 7 is a diagram illustrating an example of an overall configuration of a diagnostic imaging support system including a diagnostic imaging support apparatus according to an embodiment of the present invention.

The diagnostic imaging support system includes a diagnostic imaging support apparatus 710 and a database 722, and the apparatuses are interconnected through a communication unit 721 to allow communication. In the present embodiment, a LAN (Local Area Network) forms the communication unit 721. The database 722 manages medical images and information associated with the medical images. The diagnostic imaging support apparatus 710 acquires a medical image as a diagnosis target (diagnosis target image) managed by the database 722 and information associated with the medical image through the LAN 721.

The diagnostic imaging support apparatus 710 includes, as functional configurations, a communication IF 731, a ROM 732, a RAM 733, a storage unit 734, an operation unit 735, a display unit 736 and a control unit 737. The communication IF (interface) 731 is realized by, for example, a LAN card. The communication IF 731 manages communication between an external apparatus (for example, the database 722) through the LAN 721 and the diagnostic imaging support apparatus 710. The ROM (Read Only Memory) 732 is realized by a non-volatile memory or the like and stores various programs. The RAM (Random Access Memory) 733 is realized by a volatile memory or the like and temporarily stores various pieces of information. The storage unit 734 is realized by, for example, an HDD (Hard Disk Drive) and stores various pieces of information. The operation unit 735 is realized by, for example, a keyboard and a mouse and inputs an instruction from the user to the apparatus. The display unit 736 is realized by, for example, a display and displays various pieces of information to the user (for example, the doctor). The control unit 737 is realized by, for example, a CPU (Central Processing Unit) and comprehensively controls the process in the diagnostic imaging support apparatus 710.

The control unit 737 includes, as functional configurations, a region acquisition unit 711, an imaging finding acquisition unit 712, a characteristic value calculation unit 713, an approximate characteristic value selection unit 714, a representative characteristic value calculation unit 715, an approximate cross-sectional image acquisition unit 716, a representative cross-sectional image acquisition unit 717, a comparison unit 718 and a display processing unit 719. For example, the CPU handles the RAM 733 as a work area and reads and executes programs stored in the ROM 732 or the storage unit 734 to realize the configurations. Dedicated circuits may realize part or all of the configurations.

Based on a method described later, the region acquisition unit 711 acquires a predetermined three-dimensional region of a three-dimensional image to be diagnosed, a plurality of cross-sectional images included in the predetermined three-dimensional region and an abnormal shadow region in the predetermined three-dimensional region. The imaging finding acquisition unit 712 acquires a type and an evaluation value of an imaging finding related to the abnormal shadow from the user. The acquisition is based on, for example, an operation by the user through the operation unit 735.

The characteristic value calculation unit 713 applies image processing to the plurality of cross-sectional images acquired by the region acquisition unit 711 according to the type of the imaging finding acquired by the imaging finding acquisition unit 712. In this way, the characteristic value calculation unit 713 calculates, for each cross-sectional image, a characteristic value that can be compared with the evaluation value of the imaging finding acquired by the imaging finding acquisition unit 712.

The approximate characteristic value selection unit 714 selects a value (approximate characteristic value) closest to the evaluation value of the imaging finding from the plurality of characteristic values calculated by the characteristic value calculation unit 713. The representative characteristic value calculation unit 715 calculates a characteristic value (representative characteristic value) that represents the predetermined three-dimensional region from the plurality of characteristic values calculated from the plurality of cross-sectional images.

The approximate cross-sectional image acquisition unit 716 acquires a cross-sectional image (approximate cross-sectional image) in which the approximate characteristic value is calculated, from the plurality of cross-sectional images. The representative cross-sectional image acquisition unit 717 acquires a cross-sectional image (representative cross-sectional image) in which the representative characteristic value is calculated, from the plurality of cross-sectional images.

The comparison unit 718 compares the evaluation value of the imaging finding and the representative characteristic value to determine whether there is a significant difference between the two values. Whether there is a significant difference is determined based on, for example, whether the absolute value of the difference between the two values is greater than a predetermined threshold. The display processing unit 719 displays both the approximate cross-sectional image and the representative cross-sectional image only if a determination result indicating a significant difference in the comparison result is received from the comparison unit 718. The display processing unit 719 can display supplementary information, such as description of cross-sectional images, along with the approximate cross-sectional image and the representative cross-sectional image. The information is displayed on, for example, the screen of the display unit 736. Obviously, a printer not illustrated may print the information to display the information.

The approximate characteristic value selection unit 714 and the approximate cross-sectional image acquisition unit 716 of the functional configurations of the control unit 737 may be removed. In that case, the display processing unit 719 displays the representative cross-sectional image and the supplementary information only if the determination result indicating a significant difference in the comparison result is received from the comparison unit 718.

Figure 8:
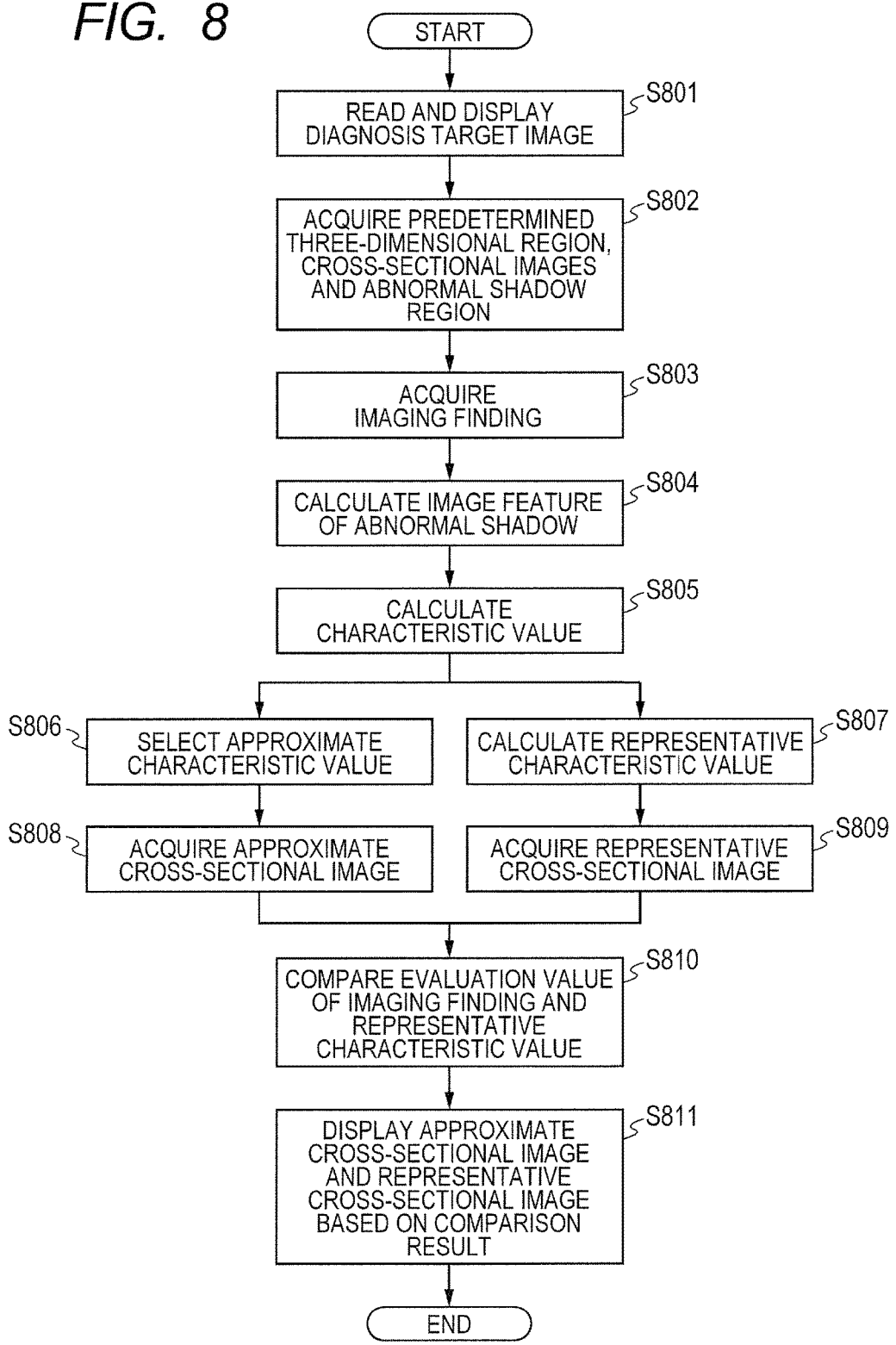
FIG. 8 is a flow chart illustrating an example of a flow of a process of a diagnostic imaging support apparatus 710.

An example of a flow of the process by the diagnostic imaging support apparatus 710 illustrated in FIG. 7 will be described with reference to FIG. 8. The process starts when the user instructs acquisition of a three-dimensional image as a diagnosis target managed on the database 722 through the operation unit 735.

When the process is started, the diagnostic imaging support apparatus 710 acquires the three-dimensional image as a diagnosis target from the database 722 through the LAN 721 according to the user instruction and stores the three-dimensional image in the RAM 733 (S801). In the diagnostic imaging support apparatus 710, the display processing unit 719 displays, on the display unit 736, an arbitrary (at a position instructed by the user) cross-sectional image included in the three-dimensional image to be diagnosed. The three-dimensional image to be diagnosed may be acquired from an external storage apparatus connected to the diagnostic imaging support apparatus 710.

The user designates a predetermined region (three-dimensional region including an abnormal shadow) of the three dimensional image as a diagnosis target through the operation unit 735. In the diagnostic imaging support apparatus 710, the region acquisition unit 711 acquires the predetermined region according to the user operation and acquires a plurality of cross-sectional images included in the predetermined region (S802). In this case, an axial cross-sectional image generated by an imaging apparatus may be acquired. A three-dimensional image may be reconfigured first, and then cross-sectional images orthogonal to an arbitrary normal direction may be created and acquired. For example, a coronal cross-sectional image and a sagittal cross-sectional image with the normal direction orthogonal to the axial cross-sectional image may be acquired. The axial cross-sectional image, the coronal cross-sectional image and the sagittal cross-sectional image will be called three orthogonal cross-sectional images.

The region acquisition unit 711 uses a known region extraction technique (such as a graph cut method and a level set method) to extract and acquire an abnormal shadow region in the predetermined region. A known abnormal shadow detection technique may be used to automatically acquire the abnormal shadow region. In this case, the abnormal shadow region is automatically acquired, and then a rectangular solid region surrounding the abnormal shadow region is automatically extracted and acquired as a predetermined three-dimensional region. A plurality of cross-sectional images included in the predetermined region is further acquired in the processing procedure.

Figure 9:
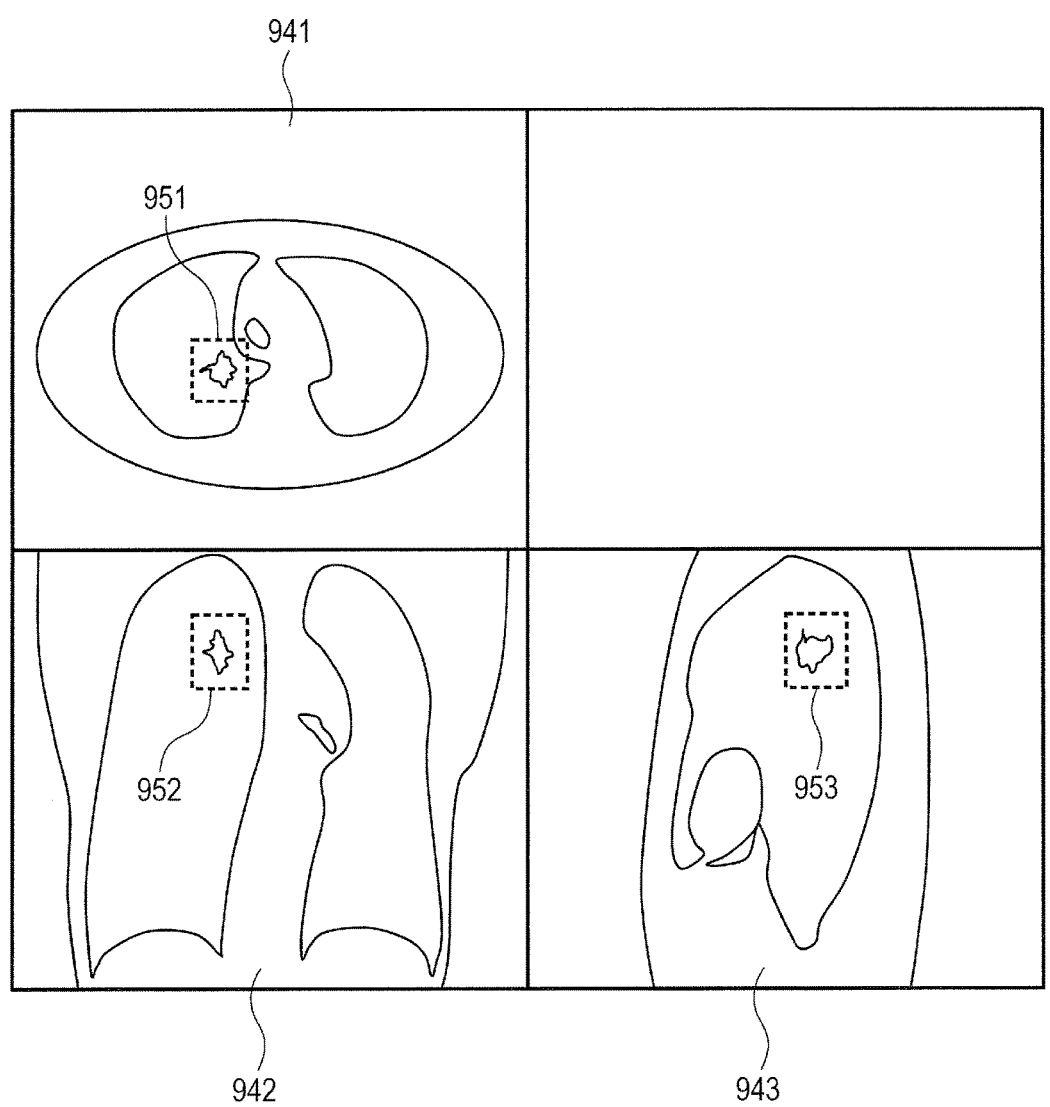
FIG. 9 illustrates examples of diagnosis target images displayed on a display unit 736.

FIG. 9 illustrates an example of the diagnosis target image displayed on the display unit 736. The display unit 736 usually cannot display the three-dimensional image. Therefore, the display unit 736 displays the axial cross-sectional image, the coronal cross-sectional image and the sagittal cross-sectional image on three image display areas 941, 942 and 943, respectively. As described, the user designates predetermined regions 951, 952 and 953 on the cross-sectional images through the operation unit 735. The predetermined regions 951, 952 and 953 are rectangular solid projection figures (rectangles) depicted on the cross-sectional images for designating a rectangular solid on the three-dimensional image. Therefore, the following relationship is established.

$$\text{X coordinate of region } 951 = \text{X coordinate of region } 952 \qquad (8)$$

$$\text{Y coordinate of region } 951 = \text{X coordinate of region } 953 \qquad (9)$$

$$\text{Y coordinate of region } 952 = \text{Y coordinate of region } 953 \qquad (10)$$

Therefore, the user can draw rectangles on two of the three orthogonal cross-sectional images to designate the predetermined region. The position of the rectangle on the remaining cross-sectional image is automatically calculated using the formulas (8) to (10). There is a plurality of cross-sectional images in each of the three orthogonal directions in the predetermined regions 951, 952 and 953. Therefore, a plurality of cross-sectional images can be acquired in any direction as a result of the process of S802.

FIG. 8 will be described again. The user inputs the imaging finding through the operation unit 735. More specifically, the user who has referenced the plurality of cross-sectional images displayed on the display unit 736 in the process of S801 inputs the type and the evaluation value of the imaging finding in relation to the abnormal shadow on the plurality of cross-sectional images. Consequently, the imaging finding acquisition unit 712 of the diagnostic imaging support apparatus 710 acquires the type and the evaluation value of the imaging finding input according to the user operation (S803). Examples of the types of the imaging finding include information related to the presence/absence or the degree of the major axis (maximum diameter) of the abnormal shadow, shape, spiculation, contour irregularity, calcification, air section, entanglement of blood vessels or bronchi, pleural indentation and air bronchogram. The process of S803 may be executed at the same time as the process of S802 or may be executed before the process of S802.

Subsequently, the characteristic value calculation unit 713 of the diagnostic imaging support apparatus 710 applies a process of S804 and S805 to each of the plurality of cross-sectional images acquired by the region acquisition unit 711. In S804, a known image processing technique is used to calculate image features of the abnormal shadow corresponding to the type of the imaging finding acquired by the imaging finding acquisition unit 712. Examples of the image features include shape features of the abnormal shadow region (such as major axis, circularity of borderline, oblateness and irregularity) and density features (an average value and dispersion of density, proportions of density values in a specific density range corresponding to calcification or air, and the like). In S805, a characteristic value that can be compared with the evaluation value of the imaging finding is calculated for each of the plurality of cross-sectional images based on the image features calculated in S804.

A calculation method of the characteristic value in the process of S805 will be described. For example, if the type of the imaging finding is "major axis", the characteristic value is obtained by measuring the major axis (maximum diameter) of an ellipse derived by applying elliptical approximation to the borderline of the abnormal shadow. If, for example, the type of the imaging finding is "contour irregularity", the characteristic value is calculated according to the size of the dispersion of distances between the center of the abnormal shadow and the points on the borderline. If, for example, the type of the imaging finding is "calcification", a density histogram of the abnormal shadow is created, and the characteristic value is calculated according to the proportion of the density value in the density range corresponding to the calcification.

In the diagnostic imaging support apparatus 710, the approximate characteristic value selection unit 714 selects a value (approximate characteristic value) closest to the evaluation value of the imaging finding acquired by the imaging finding acquisition unit 712, from the plurality of characteristic values calculated by the characteristic value calculation unit 713 (S806). However, if all characteristic values are away from the evaluation value of the imaging finding for more than a predetermined distance, the approximate characteristic value selection unit 714 may determine that there is no approximate characteristic value. In the diagnostic imaging support apparatus 710, the approximate cross-sectional image acquisition unit 716 acquires a cross-sectional image (approximate cross-sectional image) with the characteristic value selected by the approximate characteristic value selection unit 714, from the plurality of cross-sectional images acquired by the region acquisition unit 711 (S808).

Meanwhile, the representative characteristic value calculation unit 715 of the diagnostic imaging support apparatus 710 calculates a characteristic value (representative characteristic value) that represents the predetermined region acquired by the region acquisition unit 711 from the plurality of characteristic values calculated by the characteristic value calculation unit 713 (S807). Subsequently, the representative cross-sectional image acquisition unit 717 of the diagnostic imaging support apparatus 710 acquires a cross-sectional image (representative cross-sectional image) with the characteristic value calculated by the representative characteristic value calculation unit 715, from the plurality of cross-sectional images acquired by the region acquisition unit 711 (S809).

A calculation method of the representative characteristic value of S807 will be described. The calculation method of the representative characteristic value varies depending on the type of the imaging finding. For example, the maximum value of the plurality of characteristic values is set as the representative characteristic value in many types of the imaging finding, such as the major axis, spiculation, calcification, air section, entanglement of blood vessels or bronchi, pleural indentation and air bronchogram. An average value of the plurality of characteristic values is set as the representative characteristic value in part of the types of the imaging finding, such as the contour irregularity. Priorities are provided in advance to all possible values of the characteristic values, and a characteristic value with the highest priority is set as the representative characteristic value in part of the types of the imaging finding, such as the shape.

The process of S806 and S808 and the process of S807 and S809 may be executed in parallel, or one of the processes may be executed first. As in the description of FIG. 7, the approximate characteristic value selection unit 714 and the approximate cross-sectional image acquisition unit 716 can be removed from the diagnostic imaging support apparatus 710. In that case, the process of S806 and S808 is not executed.

Subsequently, the comparison unit 718 of the diagnostic imaging support apparatus 710 compares the evaluation value of the imaging finding acquired by the imaging finding acquisition unit 712 and the representative characteristic value calculated by the representative characteristic value calculation unit 715 (S810). The comparison unit 718 determines whether there is a significant difference between the two values. For example, if the two values are in a magnitude relationship, the comparison unit 718 determines that there is a significant difference when the absolute value of the difference between the two values is greater than a predetermined threshold. If, for example, the two values are not in the magnitude relationship, the comparison unit 718 determines that there is a significant difference when the two values are different. If, for example, the evaluation value of the imaging finding and/or the characteristic value is a singular value, the comparison unit 718 determines that there is a significant difference only when one of the values is a singular value.

Lastly, the display processing unit 719 of the diagnostic imaging support apparatus 710 displays the following information on the display unit 736 only if there is a significant difference between the evaluation value of the imaging finding and the representative characteristic value as a result of the comparison by the comparison unit 718 (S811). Obviously, a printer not illustrated may print the information to display the information. The information displayed on the display unit 736 includes the approximate cross-sectional image acquired by the approximate cross-sectional image acquisition unit 716 and the representative cross-sectional image acquired by the representative cross-sectional image acquisition unit 717. Supplementary information, such as description of the cross-sectional images, may also be displayed along with the cross-sectional images. If S806 and S808 are not executed, the approximate cross-sectional image and the supplementary information are not displayed.

Figure 10:
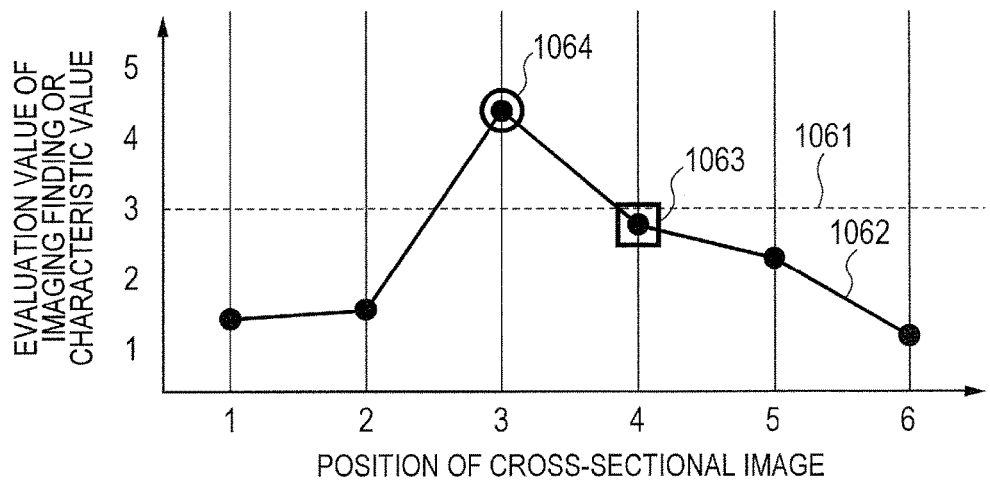
FIG. 10 is a diagram illustrating an example of a relationship between an evaluation value of an imaging finding input by a user and a characteristic value calculated by the apparatus.

FIG. 10 is a diagram illustrating an example of a relationship between the evaluation value of the imaging finding input by the user and the characteristic value calculated by the apparatus. In FIG. 10, the horizontal axis denotes positions of a plurality of cross-sectional images, and the vertical axis denotes evaluation values of the imaging finding or characteristic values. In FIG. 10, a dotted line 1061 illustrates an example of the evaluation value of the imaging finding acquired in S803. A line graph 1062 illustrates an example of the characteristic values for the plurality of cross-sectional images calculated in S805. A rectangle 1063 illustrates an example of the approximate characteristic value selected in S806. A circle 1064 illustrates an example of the representative characteristic value (1064) calculated in S807. As described, the diagnostic imaging support apparatus 710 displays the approximate cross-sectional image, the representative cross-sectional image and the supplementary information on the display unit 736 only if there is a significant difference between the evaluation value 1061 of the imaging finding and the representative characteristic value 1064.

Figure 11:
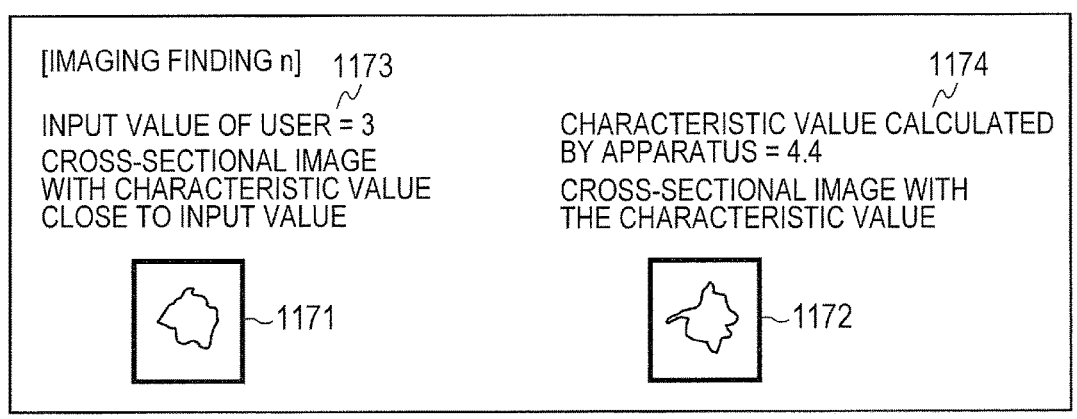
FIG. 11 is a diagram illustrating an example of an approximate cross-sectional image, a representative cross-sectional image and supplementary information of the images displayed on the display unit 736.

FIG. 11 is a diagram illustrating examples of the approximate cross-sectional image, the representative cross-sectional image and the supplementary information displayed on the display unit 736. FIG. 11 illustrates an example 1171 of the approximate cross-sectional image, an example 1172 of the representative cross-sectional image, an example 1173 of the supplementary information of the approximate cross-sectional image and an example 1174 of the supplementary information of the representative cross-sectional image. The examples of FIG. 11 are displayed on the display unit 736 because there is a significant difference (for example, difference greater than a value 1) between the evaluation value of the imaging finding ("input value of user=3") and the representative characteristic value (characteristic value calculated by apparatus=4.4"). The approximate cross-sectional image 1171 and the representative cross-sectional image 1172 are displayed for the user. Therefore, the user can check the difference between the cross-sectional images and can efficiently review the imaging finding. As a result, there is an effect that the objectivity and the reliability of the imaging finding determined by the doctor can be improved.

According to the embodiment of the present invention, the representative cross-sectional image can be displayed only if there is a significant difference between the evaluation value of the imaging finding acquired from the doctor and the representative characteristic value calculated by the diagnostic imaging support apparatus according to the present invention. Therefore, the representative cross-sectional image can be displayed as support information for prompting the doctor to review the imaging finding only if there is a doubt in the evaluation value of the imaging finding acquired from the doctor. As a result, there is an effect of improving the objectivity and the reliability of the imaging finding determined by the doctor.

Another embodiment of the present invention will be described. In diagnostic imaging of three-dimensional medical image data, a cross-sectional image (representative cross-sectional image) that most excellently expresses the features of an abnormal shadow needs to be selected from a plurality of cross-sectional images. The performance of imaging apparatuses of three-dimensional medical image data is improving year by year. The intervals between the cross-sectional images are getting smaller, and the number of cross-sectional images taken at one occasion is significantly increasing. Along with the increase in the cross-sectional images, operation of selecting an optimal representative cross-sectional image from a large number of cross-sectional images imposes a greater burden on the doctor.

The doctor had to ultimately review the cross-sectional images to select the representative cross-sectional image if the doctor determined that the automatically selected cross-sectional image was inappropriate. For example, if a plurality of imaging findings is selected as target finding items in Japanese Patent Application Laid-Open No. 2007-143982, total values of cross-sectional image selection indexes calculated for all target finding items are used to determine the representative cross-sectional image. However, the total values of the plurality of cross-sectional image selection indexes may not be appropriate indexes. Even if the plurality of cross-sectional image selection indexes are weighted and added to create new indexes, appropriate adjustment of a plurality of weights is difficult. Therefore, a problem that the burden of the doctor may not be reduced remains in the conventional technique.

Another embodiment of the present invention provides a support technique for easily selecting an optimal representative cross-sectional image for the doctor.

[Fourth Embodiment]

A diagnostic imaging support apparatus according to a fourth embodiment acquires medical information (such as information of a medical image and an electronic medical record) related to a case to be diagnosed and acquires information input by the user (such as a finding and desired cross-sectional position information) to support the diagnosis related to the case. An example of an abnormal shadow of lungs in a chest X-ray CT image will be described. Obviously, the support target is not limited to this, and the following input information is just an example for describing the steps of the process by the diagnostic imaging support apparatus.

In the following description, a plurality of types of findings obtained by the doctor from an image (for example, three-dimensional image) will be called "finding items". A finding item focused by the doctor will be called a "target finding item". A plurality of possible states of the finding item will be called "values of finding". The values of finding are values in various ranges depending on the corresponding finding item. In an example of the present embodiment, the finding items illustrated in Table 1 can be input or acquired, and the finding items can have the values of finding as illustrated in Table 1. Whether the finding items are the target finding items can also be input or acquired. For example, "Shape" indicates the shape of the abnormal shadow, and three states of "Spherical", "Lobular" and "Irregular" are possible. "Circle" indicates the degree of roundness of the abnormal shadow. "Spiculation" indicates the degree of the length or the number of spiculations in the abnormal shadow. "Involvement (vessels)" indicates presence/absence of the entanglement of blood vessels in the abnormal shadow.

Figure 12:
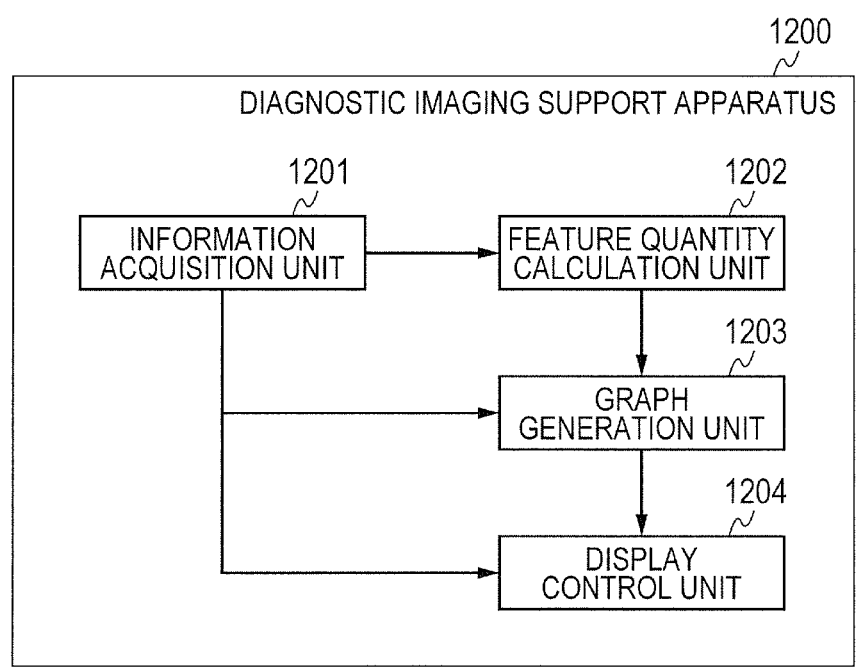
FIG. 12 is a diagram illustrating a device configuration example of a diagnostic imaging support apparatus according to an embodiment of the present invention.

FIG. 12 illustrates a configuration of the diagnostic imaging support apparatus according to the fourth embodiment. A diagnostic imaging support apparatus 1200 includes an information acquisition unit 1201, a feature quantity calculation unit 1202, a graph generation unit 1203 and a display control unit 1204.

The information acquisition unit 1201 acquires the medical information of the case, the information input by the user and one or more target finding items and outputs the information and the items to the feature quantity calculation unit 1202, the graph generation unit 1203 and the display control unit 1204. The feature quantity calculation unit 1202 calculates feature quantities corresponding to the target finding items for each cross-sectional position of the medical image based on the medical information and one or more target finding items acquired by the information acquisition unit 1201. The calculated feature quantities are output to the graph generation unit 1203 in association with the cross-sectional positions.

The graph generation unit 1203 generates a graph based on the feature quantities at each cross-sectional position calculated by the feature quantity calculation unit 1202 and based on the information input by the user and one or more target finding items acquired by the information acquisition unit 1201. The generated graph is output to the display control unit 1204. The display control unit 1204 displays the graph generated by the graph generation unit 1203 and the cross-sectional images corresponding to the cross-sectional positions acquired by the information acquisition unit 1201.

Figure 1:
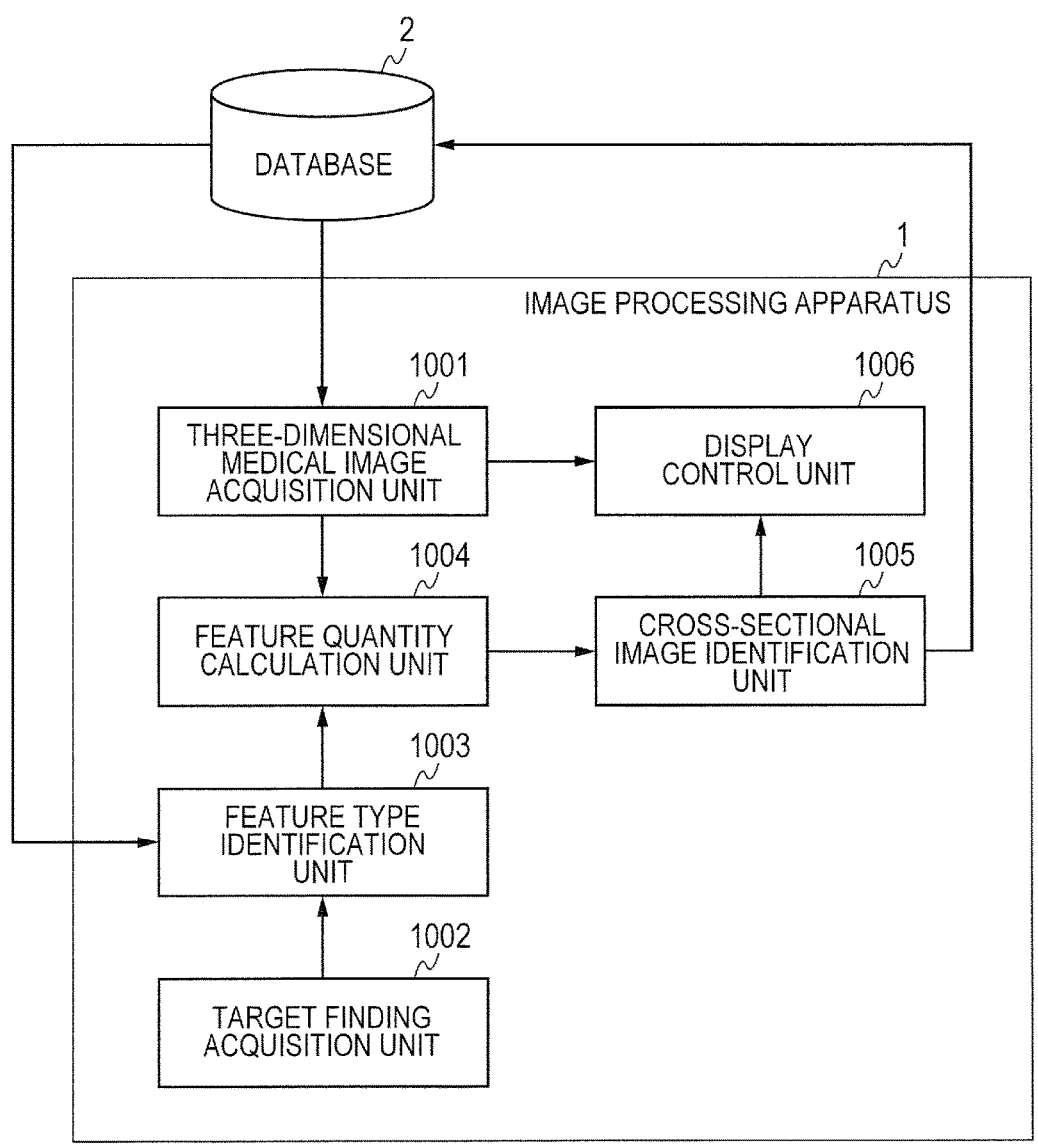
FIG. 1 is a diagram illustrating a device configuration example of an image processing apparatus according to a first embodiment.

At least part of the components of the diagnostic imaging support apparatus 1200 illustrated in FIG. 1 may be realized as independent apparatuses. The components may be realized by software that realizes the functions. It is assumed in the present embodiment that the components are realized by software.

Figure 13:
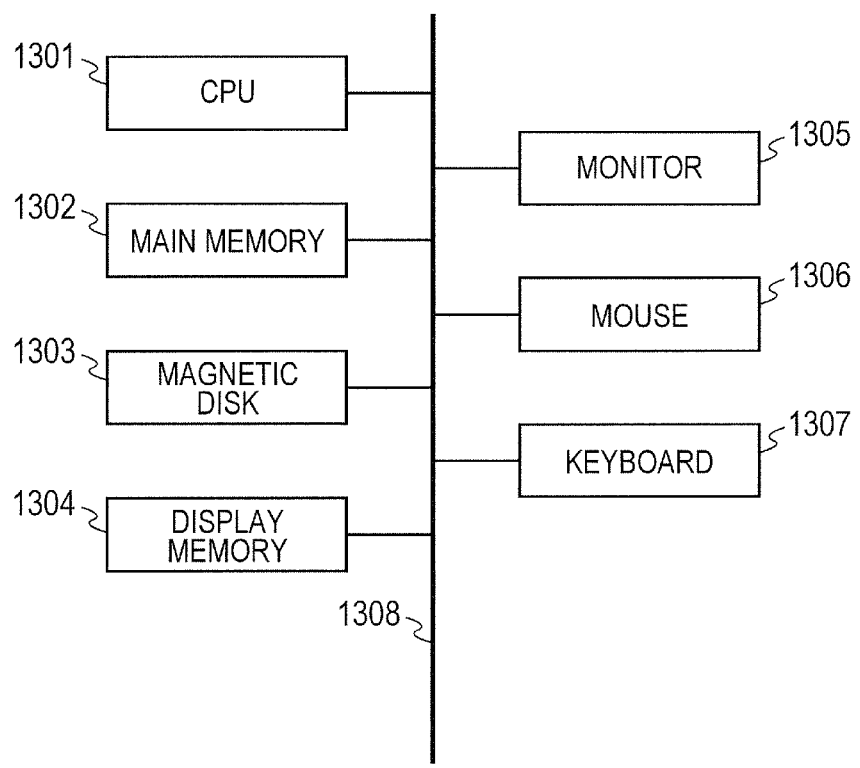
FIG. 13 is a diagram illustrating a basic configuration of a computer that realizes, by software, components of the diagnostic imaging support apparatus according to an embodiment of the present invention.

FIG. 13 is a diagram illustrating a basic configuration of a computer that executes the software to realize the functions of the components illustrated in FIG. 12. A CPU 1301 mainly controls operation of the constituent elements. A main memory 1302 stores a control program executed by the CPU 1301 and provides an operation region for the CPU 1301 to execute the program. A magnetic disk 1303 stores an operating system (OS), a device drive of a peripheral device, and various types of application software including a program for executing a process described later. A display memory 1304 temporarily stores display data. A monitor 1305 is, for example, a CRT monitor or a liquid crystal monitor, and displays images and texts based on data from the display memory 1304. A mouse 1306 and a keyboard 1307 are for pointing input and input of characters by the user. A common bus 1308 interconnects the constituent elements to allow communication.

A general computer and peripheral apparatuses can be used to form the device configuration. A control procedure of the diagnostic imaging support apparatus 1200 according to the present invention described later with reference to FIG. 15 can be realized as a program executed on the computer.

Figure 14:
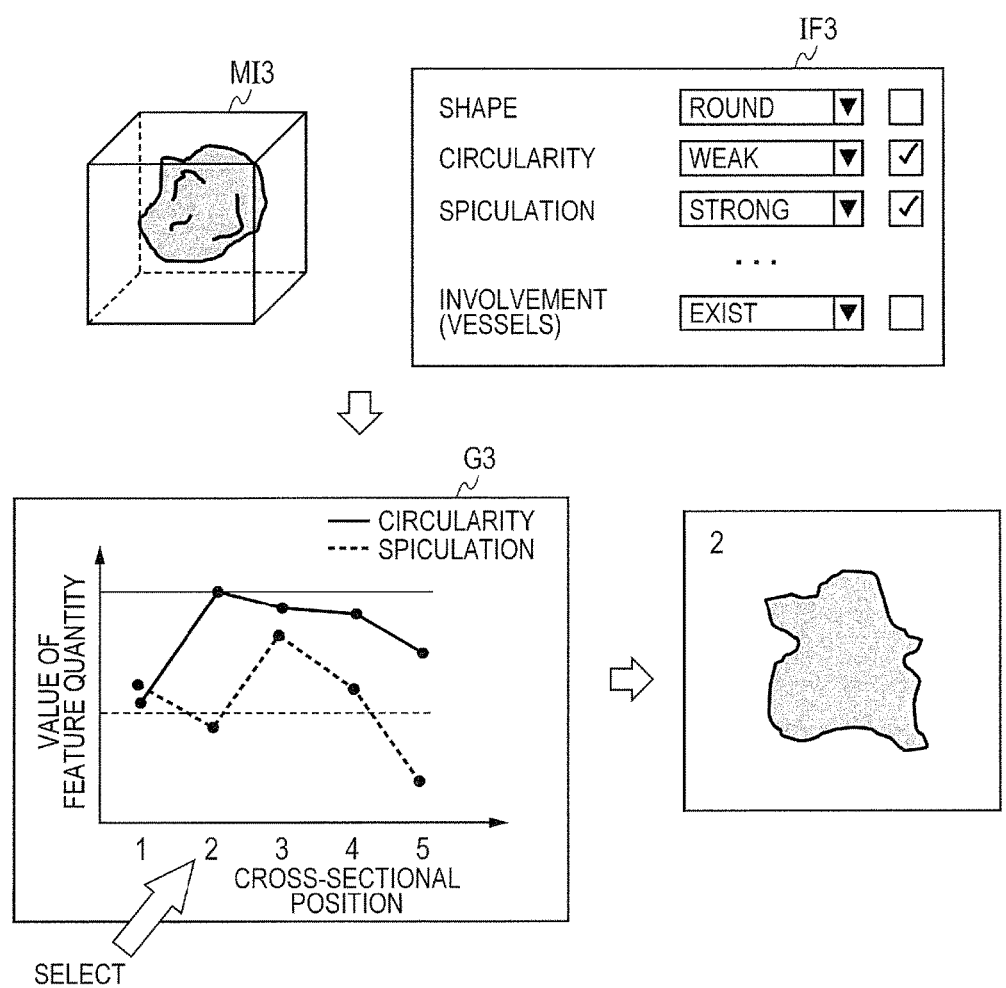
FIG. 14 is a diagram illustrating a summary of a processing procedure of a diagnostic imaging support apparatus 1200.

FIG. 14 illustrates a summary of the present embodiment. "MI3" denotes a three-dimensional image to be diagnosed (three-dimensional medical image). In the present embodiment, a three-dimensional image of a region of interest (ROI) including the target abnormal shadow is acquired as a three-dimensional medical image. A cross-sectional image at a cross-sectional position p is designated with "$I_p$" here. In the present embodiment, cross-sectional images in axial tomography (for example, cross-sectional images generated at 1 mm intervals) are designated with "$I_p$". In FIG. 14, "p" is in a range of 0 to 5. "IF3" denotes an input area of the values of finding displayed on the monitor 1305. The user can input the values of finding for the finding items from a pull-down menu of "IF3". The user can also check the check boxes corresponding to the finding items to input the target finding items. When the target finding items are input, the diagnostic imaging support apparatus 1200 identifies the feature quantities associated in advance with the finding items and calculates the feature quantities for the cross-sectional images at the cross-sectional positions. The cross-sectional positions and the feature quantities are associated to generate a graph. The values of finding input by the doctor are converted to the corresponding feature quantities, and the feature quantities are displayed on the graph. "G3" is an example of the graph generated by the process. The diagnostic imaging support apparatus 1200 displays the graph G3 on the monitor 1305. The user can reference the displayed graph to select, on the graph, a cross-sectional position to be displayed. When the cross-sectional position is selected, the monitor 1305 displays the cross-sectional image at the cross-sectional position.

For the values of finding in the example of FIG. 14, "Spherical" is input to "Shape", "Weak" is input to "Circularity", "Strong" is input to "Spiculation", and "Exist" is input to "Involvement (vessels)". "Circularity" and "Spiculation" are further input as target finding items. In this case, the diagnostic imaging support apparatus 1200 identifies the feature quantities associated with the "Circularity" and "Spiculation" as the target finding items and calculates the feature quantities at each cross-sectional position. The graph is generated based on the result. "Circularity: Weak" and "Spiculation: Strong" that are the values of finding input by the user for the target finding items are converted to corresponding feature quantities and displayed on the graph. A cross-sectional image at the cross-sectional position selected by the user on the graph (cross-sectional image $I_2$ if the user selects "Cross-sectional Position: 2") is displayed.

Figure 15:
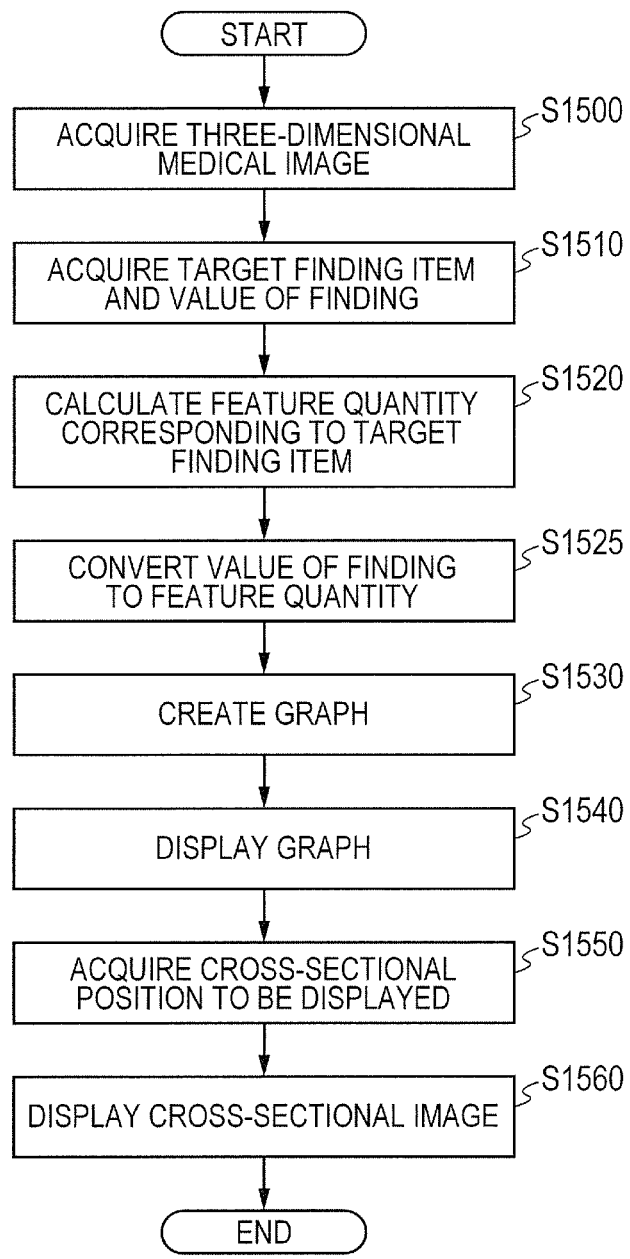
FIG. 15 is a flow chart illustrating an example of a flow of a process of the diagnostic imaging support apparatus 1200.

FIG. 15 is a flow chart of the present embodiment. A specific processing procedure executed by the diagnostic imaging support apparatus 1200 will be described with reference to the flow chart.

In step S1500, the information acquisition unit 1201 acquires a three-dimensional medical image from a database not illustrated. In the present embodiment, it is assumed that a three-dimensional image of a region of interest including a target abnormal shadow is acquired as the three-dimensional medical image. A three-dimensional medical image including a region other than the region of interest may be acquired from the database. In that case, for example, the user can designate a region of interest from the three-dimensional medical image through a GUI not illustrated, and the region of interest may be used as the three-dimensional medical image handled in the process of a later stage.

In step S1510, the information acquisition unit 1201 acquires information obtained by the diagnosis of the three-dimensional medical image by the user acquired in step S1500. Specifically, one or more target finding items input by the user and the values of finding in the target finding items are acquired. The user uses, for example, an imaging finding input form as illustrated by "IF3" of FIG. 14 to input the items and the values.

In step S1520, the feature quantity calculation unit 1202 calculates feature quantities corresponding to the target finding items acquired in step S1510, for each tomographic position of the three-dimensional medical image. For example, when "Circularity" and "Spiculation" are the target finding items, feature quantities $I_{co}$ and $I_{su}$ corresponding to the finding items are calculated by the following process. A threshold is determined by discriminant analysis from a histogram of the three-dimensional medical image, and a binarization process is applied to generate a three-dimensional binary image. The feature quantities are calculated for images at the cross-sectional positions (binary cross-sectional images) in the generated binary image based on the following formulas.

Circularity $$I_{co} = w_1 * C$$

Spiculation $$I_{su} = w_2 * L - w_3 * F$$

"C" denotes circularity, "L" denotes a contour line length, and "F" denotes a filling factor. The circularity and the filling factor are calculated by the following formulas. The contour line length is a length of a contour line of a target region described later.

Circularity $$C = 4\pi * \left(\frac{\text{Area}}{L^2}\right)$$

Filling Factor $$F = \frac{\text{Area}}{Feret_h * Feret_v}$$

"Area" denotes an area of each region in the binary cross-sectional images. "$Feret_h$" denotes a horizontal direction Feret diameter, and "$Feret_v$" denotes a vertical direction Feret diameter. The diameters are calculated from a bounding rectangle of each region in the binary cross-sectional images. Furthermore, "$w_i$" denotes a predetermined weight, and "$w_i$" is adjusted so that "$I_{co}$" and "$I_{su}$" fall within a range of 0 to 1.0.

The process described above is an example of a process of calculating "$I_{co}$" and "$I_{su}$", and the process is not limited to this. Even if finding items other than "Circularity" and "Spiculation" (such as "Shape" and "Involvement (vessels)" in the example of Table 1) are the target finding items, the feature quantities corresponding to the target finding items are calculated from the cross-sectional images. The feature quantities can be any values strongly correlated to the values of finding.

In step S1525, the feature quantity calculation unit 1202 converts the values of finding in the target finding items acquired in step S1510 to values equivalent to the feature quantities of the finding items. For example, the values of finding of "Circularity" and "Spiculation" are converted to feature quantities ($I_{co}$, $I_{su}$) based on the following correspondence.

Circularity ($I_{co}$) Strong: 0.9, Medium: 0.6, Weak: 0.25, None: 0.05

Spiculation ($I_{su}$) Strong: 0.9, Medium: 0.6, Weak: 0.25, None: 0.05

The conversion from the values of finding to the feature quantities is not limited to the above process. For example, sets of the values of finding and the feature quantities may be obtained for a large number of cross-sectional images, and a neural network for delivering the feature quantities from the values of finding through learning that handles the sets as input may be generated in advance. The neural network may be used for the conversion.

Figure 16:
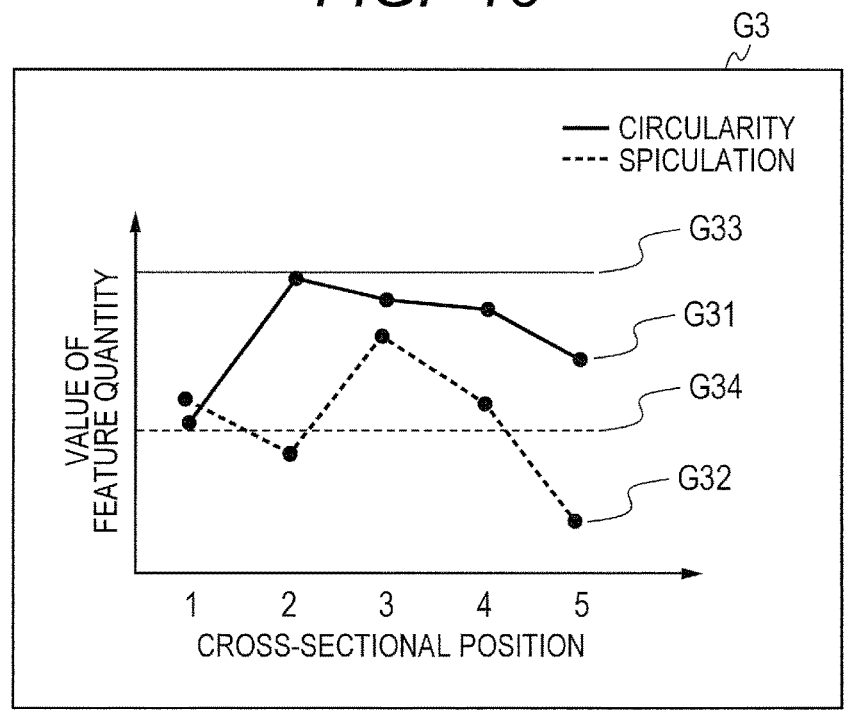
FIG. 16 is a diagram showing an example of a graph illustrating a relationship between acquired findings and feature quantities of cross-sectional images calculated by the diagnostic imaging support apparatus 1200.

In step S1530, the graph generation unit 1203 generates a graph based on the feature quantities calculated from the cross-sectional images in step S1520 and based on the feature quantities obtained by converting the values of finding in step S1525. In the present embodiment, the vertical axis indicates the values of the feature quantities, and the horizontal axis indicates the cross-sectional images $I_p$. The feature quantities at the cross-sectional positions are plotted. The feature quantities obtained by converting the values of finding are superimposed using lines parallel to the horizontal axis. FIG. 16 illustrates an example of the graph generated in the present embodiment. In the graph, the vertical axis denotes the values of the feature quantities, and the horizontal axis denotes the cross-sectional positions. "G31" and "G32" are line graphs plotting, on the graph, the feature quantities calculated from the cross-sectional images at the cross-sectional positions. "G33" and "G34" are values obtained by converting the values of finding input by the user to the feature quantities. If the graph is generated for a plurality of finding items, the types of the lines may also be displayed so that the finding items can be recognized. In FIG. 16, a graph corresponding to "Circularity" is displayed by a solid line, and a graph corresponding to "Spiculation" is displayed by a dotted line.

In step S1540, the display control unit 1204 displays the graph generated in step S1530. In step S1550, the information acquisition unit 1201 acquires the cross-sectional position of the cross-sectional image to be displayed. In the present embodiment, the user checks the graph displayed in step S1540 and inputs the cross-sectional position to be displayed, through a GUI not illustrated. The method of acquiring the cross-sectional position is not limited to this. For example, the user may select a point on the graph to acquire the cross-sectional position corresponding to the point. In step S1560, the display control unit 1204 displays the cross-sectional image at the cross-sectional position acquired in step S1550.

In this way, according to the diagnostic imaging support apparatus of the present embodiment, the feature quantities calculated at the cross-sectional positions and the values of finding input by the user in relation to the target finding items are illustrated on top of each other. As a result, the user can easily figure out how much the cross-sectional images match the values of finding focused by the user. In addition, a plurality of target finding items is expressed by one graph to easily figure out the relationship between the target findings. Therefore, the user can easily perform operation of selecting the representative cross-sectional image optimal for the user, in which the target findings are taken into account, from the plurality cross-sectional images

[Fifth Embodiment]

Examples obtained by partially modifying the fourth embodiment will be illustrated. The other parts are the same as in the first embodiment, and the description will not be repeated.

<Modified Example 1>

In step S1510, the target finding items are acquired through input by the user. However, the target finding items may be acquired by another method. For example, an identifier may be constructed based on learning using sets of the feature quantities and the target finding items obtained for a past diagnosis result or sets of the values of finding and the target finding items to select the target finding items from the image feature quantities or the values of finding. According to the method, the target finding items can be automatically set according to the input by the user. Therefore, the burden of the user can be reduced.

<Modified Example 2>

Figure 17:
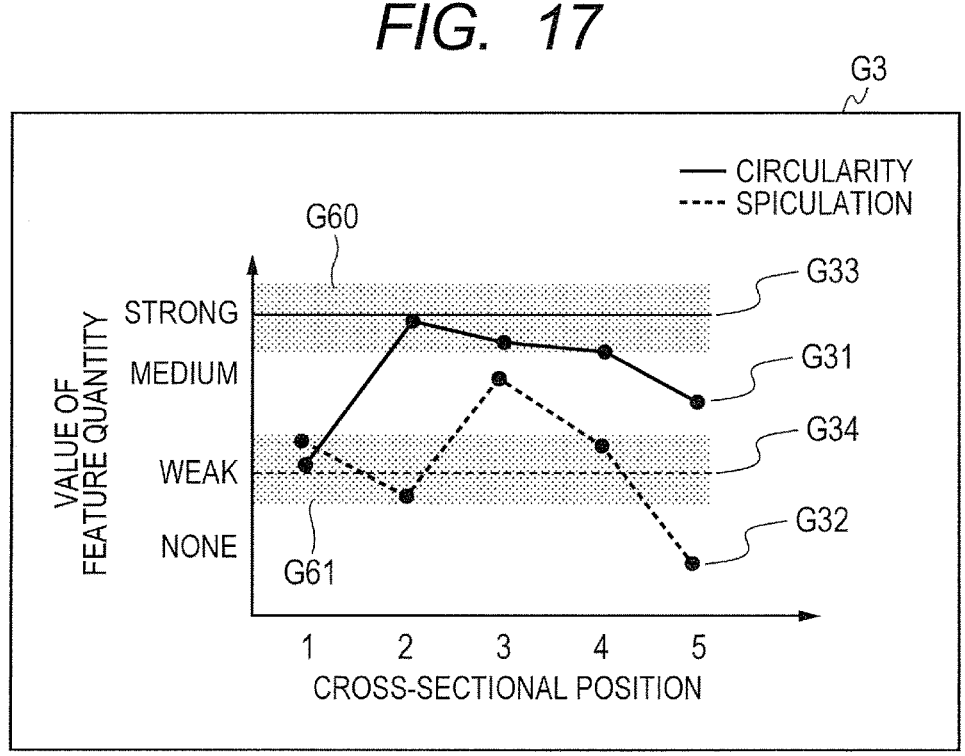
FIG. 17 is a diagram showing a modified example of a graph illustrating a relationship between acquired findings and feature quantities of cross-sectional images calculated by the diagnostic imaging support apparatus 1200.

In step S1525, the values of finding input by the user are converted to single values of feature quantities. However, the values may be converted to specific ranges, without converting the values to single values of feature quantities. In this case, the ranges of the feature quantities corresponding to the values of finding may be displayed in band shapes as illustrated for example in FIG. 17. "G60" illustrates a band shape of a range $(1.0 \geq I_{co} > 0.8)$ in which the finding conversion index in the finding item "Circularity" is "Strong". "G61" illustrates a band shape of a range $(0.4 \geq I_{sti} > 0.1)$ in which the finding conversion index in the finding item "Spiculation" is "Weak". According to the method, to which of the values of the target finding items the feature quantities (G31, G32) calculated by the computer correspond are visually displayed. Therefore, the determination by the user can be more accurate.

<Modified Example 3>

The method of selecting the cross-sectional images for calculating the feature quantities is not limited to the method described above (axial cross-sectional images). For example, the feature quantities may be calculated for coronal or sagittal cross-sectional images. The cross-sectional images may be created in free directions to calculate the feature quantities. For example, an x axis, a y axis and a z axis passing through the center of the image may be set, and one or two of the axes may be set as rotation centers. The feature quantities may be calculated from the cross-sectional images obtained by rotating the image by 10 degrees each for 180 degrees. In this case, serial numbers can be set to the cross-sectional image, and the graph can be arranged in the order of the numbers.

<Modified Example 4>

In step S1530, the vertical axis of the graph indicates the values of the feature quantities. However, the vertical axis of the graph may indicate the values of finding to generate the graph. In this case, the feature quantities calculated in step S1520 are converted to the values of finding. For example, an identifier may be constructed through learning based on sets of the feature quantities and the values of finding in a large number of past cross-sectional images to convert the feature quantities to the values of finding. According to the method, the feature quantities are uniquely converted to the values of finding. Therefore, the doctor can more easily understand which cross-sectional image excellently expresses which finding item.

The embodiment facilitates viewing the relationship between the values of finding in the target finding items input by the doctor and the feature quantities corresponding to the finding items calculated for the cross-sectional images by the diagnostic imaging support apparatus according to the present invention. The doctor can easily recognize the degree of closeness of the features of the cross-sectional images to the values of finding input by the doctor. Therefore, the doctor can easily select the representative cross-sectional image with reference to the display. Even if a plurality of imaging findings are selected as the target finding items, the doctor can easily figure out the relationship between the plurality of target finding items just by looking at the drawing. Therefore, the selection of the representative cross-sectional image is facilitated. As a result, there are fewer cases in which the doctor is not certain about selecting the cross-sectional image to be attached to the diagnostic imaging report, and there is an effect of reducing the burden of the doctor.

TABLE 1

| j | Finding Item | Value of Finding |
|---|---|---|
| 1 | Shape | Round |
|   |   | Lobular |
|   |   | Irregular |
| 2 | Circularity | Strong |
|   |   | Medium |
|   |   | Weak |
|   |   | None |
| 3 | Spiculation | Strong |
|   |   | Medium |
|   |   | Weak |
|   |   | None |
|   | ... |   |
| m | Involvement (vessels) | Exist |
|   |   | Doubt |
|   |   | None |

The following process can also be executed to realize the apparatus according to the embodiments of the present invention. In the process, software (program) for realizing the functions of the embodiments is supplied to a system or an apparatus through a network or various storage media, and a computer (or CPU or MPU) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-167257, filed Jul. 29, 2011, which is hereby incorporated by reference herein in its entirety.

What is claimed is:

1. An image processing apparatus comprising:
a memory storing a program; and
one or more processors which, by executing the program, function as:
a finding acquisition unit configured to acquire a plurality of target findings in a three-dimensional medical image;
an inference unit configured to calculate a contribution of each target finding to an inferred diagnosis;
a selection unit configured to select a target finding according to the contribution calculated with the highest probability to the inferred diagnosis among the plurality of target findings; and
an identification unit configured to identify at least one cross-sectional image from the three-dimensional medical image based on a feature amount associated with the selected target finding.

2. The image processing apparatus according to claim 1, wherein the identification unit is configured to identify the at least one cross-sectional image from the three-dimensional medical image based on a feature amount representing a value indicating a feature of the selected finding.

3. The image processing apparatus according to claim 1, wherein the one or more processors, by executing the program, further function as a calculation unit configured to calculate contribution indicating degree of contribution to the inference of the diagnosis for each finding used for the inference.

4. The image processing apparatus according to claim 3, wherein the selection unit is configured to select a finding having the contribution equal to or greater than a threshold as the finding which has contributed to the inference of the diagnosis.

5. The image processing apparatus according to claim 3, wherein the selection unit is configured to select a finding having the greatest contribution as the finding which has contributed to the inference of the diagnosis.

6. The image processing apparatus according to claim 3, wherein the calculation unit is configured to calculate the contribution of the finding using difference between an inferred probability of the diagnosis with the finding and an inferred probability of the diagnosis without the finding.

7. The image processing apparatus according to claim 1, wherein the one or more processors, by executing the program, further function as a reception unit to receive an input of a diagnosis from a user,
wherein the selection unit is configured to select a finding which has contributed to the inference of the input diagnosis if the input diagnosis differs from the inferred diagnosis.

8. The image processing apparatus according to claim 1, wherein the one or more processors, by executing the program, further function as a display control unit configured to display the identified cross-sectional image on a display.

9. The image processing apparatus according to claim 1, wherein a cross-sectional direction of the cross-sectional image is any one of an axial direction, a coronal direction, or a sagittal direction, or a free direction.

10. An operating method of an image processing apparatus comprising:
acquiring a plurality of target findings in a three-dimensional medical image;
calculating a contribution of each target finding to an inferred diagnosis;
selecting a target finding according to the contribution calculated with the highest probability to the inferred diagnosis among the plurality of target findings; and
identifying at least one cross-sectional image from the three-dimensional medical image based on a feature amount associated with the selected target finding.

11. A non-transitory computer-readable storage medium storing a program for causing a computer to execute the operating method according to claim 10.

12. The image processing apparatus according to claim 1, wherein the identification unit is configured to calculate a feature amount associated with the selected finding in each cross-sectional image to identify the at least one cross-sectional image.

13. The image processing apparatus according to claim 3, wherein the calculation unit is configured to calculate the contribution of the finding in the diagnosis for all findings in the three-dimensional medical image.

* * * * *